United States Patent
Goldfarb et al.

(10) Patent No.: US 11,666,463 B2
(45) Date of Patent: *Jun. 6, 2023

(54) STAIR DESCENT CONTROL FOR POWERED LOWER LIMB DEVICES

(71) Applicant: Vanderbilt University, Nashville, TN (US)

(72) Inventors: Michael Goldfarb, Franklin, TN (US); Brian Lawson, Nashville, TN (US); Atakan Huseyin Varol, Astana (KZ)

(73) Assignee: Vanderbilt University, Nashville, TN (US)

( * ) Notice: Subject to any disclaimer, the term of this patent is extended or adjusted under 35 U.S.C. 154(b) by 15 days.

This patent is subject to a terminal disclaimer.

(21) Appl. No.: 17/499,287

(22) Filed: Oct. 12, 2021

(65) Prior Publication Data
US 2022/0054285 A1 Feb. 24, 2022

Related U.S. Application Data

(62) Division of application No. 16/502,914, filed on Jul. 3, 2019, now Pat. No. 11,173,054, which is a division
(Continued)

(51) Int. Cl.
*A61F 2/70* (2006.01)
*A61F 2/64* (2006.01)
(Continued)

(52) U.S. Cl.
CPC .......... *A61F 2/70* (2013.01); *A61F 2/60* (2013.01); *A61F 2/64* (2013.01); *A61F 2/6607* (2013.01);
(Continued)

(58) Field of Classification Search
CPC ...... A61F 2/64; A61F 2/68; A61F 2/70; A61F 2002/701; A61F 2002/704; A61F 2002/7625; A61F 2002/7635
See application file for complete search history.

(56) References Cited

U.S. PATENT DOCUMENTS

| 4,685,925 A | 8/1987 | Childress |
| 5,571,205 A | 11/1996 | James |

(Continued)

FOREIGN PATENT DOCUMENTS

| GB | 2252503 | 3/1988 |
| WO | WO 2010/088635 | 8/2010 |

OTHER PUBLICATIONS

Au et al., "Powered ankle-foot prosthesis improves walking metabolic economy," IEEE Transactions on Robotics (2009) 25: 51-66.
(Continued)

*Primary Examiner* — Christie Bahena
(74) *Attorney, Agent, or Firm* — Nixon Peabody LLP

(57) ABSTRACT

Systems and methods of operating a lower limb device having at least a powered joint are provided. A method includes configuring the device to a first state in a finite state model for a current activity mode including a stair ascent mode or a stair descent mode. The method also includes, based on real-time sensor information, transitioning the device between different states in the finite state model when pre-defined criteria for transitioning among the different states are met. In the method, the finite state model for stair ascent includes lifting and swing phases, where the lifting phase includes a powered knee extension and a powered ankle push-off. The finite state model for stair descent includes yielding and swing states, where the swing states include providing a powered plantarflexion of the powered ankle joint and the yielding states include providing a resistive and passive plantarflexion of the powered ankle joint.

5 Claims, 28 Drawing Sheets

Related U.S. Application Data of application No. 13/832,431, filed on Mar. 15, 2013, now Pat. No. 10,441,439.

(60) Provisional application No. 61/647,369, filed on May 15, 2012.

(51) Int. Cl.
*A61F 2/60* (2006.01)
*A61F 2/76* (2006.01)
*A61F 2/66* (2006.01)

(52) U.S. Cl.
CPC ... *A61F 2002/607* (2013.01); *A61F 2002/701* (2013.01); *A61F 2002/704* (2013.01); *A61F 2002/7625* (2013.01); *A61F 2002/7635* (2013.01)

(56) References Cited

U.S. PATENT DOCUMENTS

| | | |
|---|---|---|
| 6,517,585 B1 | 2/2003 | Zahedi |
| 8,057,410 B2 | 11/2011 | Angold |
| 8,419,804 B2 | 4/2013 | Herr |
| 2005/0010265 A1 | 1/2005 | Baru Fassio |
| 2005/0251079 A1 | 11/2005 | Carvey |
| 2007/0050044 A1 | 3/2007 | Haynes |
| 2009/0171468 A1 | 7/2009 | Pusch |
| 2009/0222105 A1 | 9/2009 | Clausen |
| 2009/0265018 A1 | 10/2009 | Goldfarb |
| 2010/0023133 A1 | 1/2010 | Fairbanks |
| 2010/0179668 A1 | 7/2010 | Herr |
| 2010/0185124 A1 | 7/2010 | Bisbee |
| 2011/0224803 A1 | 9/2011 | Goldfarb |
| 2011/0257764 A1 | 10/2011 | Herr |
| 2012/0083901 A1 | 4/2012 | Langlois |
| 2012/0221120 A1 | 8/2012 | Seyr |
| 2012/0259429 A1 | 10/2012 | Han |
| 2012/0259431 A1 | 10/2012 | Han |
| 2013/0197408 A1 | 8/2013 | Goldfarb |

OTHER PUBLICATIONS

Au et al., "Powered ankle-foot prosthesis to assist level-ground and stair descent gaits," Neural Netw (2008) 21: 654-666.

Bellmann et al., "SPARKy 3: Design of an active robotic ankle prosthesis with two actuated degrees of freedom using regenerative kinetics," Biomedical Robotics and Biomechanics (2008): 511-516.

Bellmann et al., "Comparative biomechanical analysis of current microprocessor-controlled prosthetic knee joints," Arch Phys Med Rehabil (2010) 91: 644-652.

Blumentritt et al., "The safety of C-Leg: Biomechanical tests," Journal of Prosthetics and Orthotics (2009) 21(1): 2-15.

Chin et al., "Effect of an intelligent prosthesis (IP) on the walking ability of young transfemoral amputees," American Journal of Physical Medicine & Rehabilitation (2003) 82(6): 447-451.

Datta et al., "A comparative evaluation of oxygen consumption and gait pattern in amputees using Intelligent Prostheses and conventionally damped knee swing-phase control," Clin Rehabil (2005) 19: 398-403.

Duncan et al., "Six degree of freedom joint power in stair climbing," Gait & Posture (1997) 5: 204-210.

Hitt et al., "An active foot-ankle prosthesis with biomechanical energy regeneration," Journal of Medical Devices (2010) 4: 0011003-1 to 011003-9.

Johnasson et al., "A clinical companson of variable-damping and mechanically passive prosthetic knee devices," Am J Phys Med Rehabil (2005) 84: 563-575.

Koganezawa et al., "Multifunctional above-knee prosthesis for stairs walking," Prost Ortho Int (1987) 11: 139-145.

Lawson et al., "Standing stability enhancement with an intelligent powdered trasnfemoral prosthesis," IEEE Trans Biomed Eng (2011) 58: 2617-2624.

Lewis et al., "Walking with increased ankle pushoff decreases hip muscle moments," Journal of Biomechanics (2008) 41: 2082-2089.

McFayden et al., "An integrated biomechanical analysis of normal stir ascent and descent," J Biomechanics (1988) 21(9): 733-744.

Reid et al., "Knee biometrics of alternate stair ambulation patterns," Medicine & Science in Sports & Exercise (2007): 2005-2011.

Riener et al., "Stair ascent & descent at different inclinations," Gait & Posture (2002) 15: 32-44.

Schmalz et al., "Biomechanical analysis of stair ambulation in lower limb amputees," Gait & Posture (2007) 25: 267-278.

Segal et al., "Kinematic and kinetic comparisons of transfemoral amputee gait using C-Leg® and Mauch SNS® prosthetics knees," Journal of Rehabilitation Research & Development (2006) 43(7):857-870.

Sup et al., "Preliminary evaluations of a self-contained anthropomorphic transfemoral prosthesis," IEEE ASME Trans Mechatron (2009) 14: 667-676.

Sup et al., "Upslope walking with a powered knee and ankle prosthesis: Initial results with an amputee subject," IEEE Transactions on Neural Systems and Rehabilitation Engineering (2011) 19(1): 71-78.

Varol et al., "Multiclass real-time intent recognition of a powered lower limb prosthesis," IEEE Transactions on Biomedical Engineering (2010) 57(3): 542-551.

Zachazewski et al., "Biomechanical analysis of body mass transfer during stair ascent and descent of healthy subjects," Journal of Rehabilitation Research & Development (1993) 30(4): 412-422.

Tsai, Lung-Wen, "Robot Analysis: The Mechanics of Serial and Parallel Manipulators," L.-W (1999) pp. 54-76.

R. D. Gregg, T. Lenzi. L. J. Hargrove, and J. W. Sensinger, "Virtual Constraint Control of a Powered Prosthetic Leg: From Simulation to Experiments with Transfemoral Amputees," in IEEE Transactions on Robotics, vol. 30, No. 6, pp. 1455-1471, Dec. 2014.

Novak, Alison, "Stair Negotiation Alters Stability in Older Adults," October 210. Lower Extremity Review.

Bellmann, Malte (1 and 2), "Stair ascent with an innovative microprocessor-controlled exoprosthetic knee joint," Published online Jan. 14, 2012. Biomed tech 2012.

Ottobock. C-leg instructions brochure. Dated pre-2011.

STAIR DESCENT CONTROL FOR POWERED LOWER LIMB DEVICES

CROSS-REFERENCE TO RELATED APPLICATIONS

This application is a division of U.S. patent application Ser. No. 16/502,914, filed on Jul. 3, 2019, which is now allowed; U.S. patent application Ser. No. 16/502,914 is a division of U.S. patent application Ser. No. 13/832,431, filed Mar. 15, 2013, which issued as U.S. Pat. No. 10,441,439 on Oct. 15, 2019, which claims priority to and the benefit of U.S. Provisional Patent Application No. 61/647,369, filed May 15, 2012, entitled "METHOD FOR CONTROL OF STAIR ASCENT AND DESCENT IN A POWERED KNEE AND ANKLE PROSTHESIS", the contents of which are herein incorporated by reference in their entirety.

FIELD OF THE INVENTION

The present invention relates to control of powered lower limb devices, and more specifically to apparatus and methods for stair ascent and descent control for powered lower limb devices.

BACKGROUND

Over the past two to three decades, two significant technological advances have helped to enhance the mobility of transfemoral amputees. In the 1980s, the introduction of composites such as carbon fiber allowed the creation of energy-storing ankle-foot complexes that can return some of the energy stored in the stance phase of gait back to the limb for the swing phase. In the 1990s, the integration of microprocessor control with modulated damping elements in prosthetic knee joints enhanced the capability of prosthetic knees to accommodate variation in gait speed and locomotion activity. Despite these advances, the capabilities of these joints remain inferior relative to a healthy joint in a sound leg of an amputee, particularly during stair ascent and descent.

The inability to provide biomechanically healthy stair ascent is largely due to the fact that the emulation of healthy stair ascent requires significant net positive power at the knee and ankle joints. An energetically passive prosthesis is fundamentally unable to provide such net power at either joint. However, it should be noted that the inability of existing prostheses to provide biomechanically healthy stair descent is not due to a lack of power generation capability, per se, but rather due to the inability of existing prostheses to appropriately configure the ankle joint prior to foot strike.

Stair descent is characterized by forefoot strike rather than heel strike, which enables the ankle joint to dissipate substantial power during the loading phase of gait. A typical passive (compliant) ankle/foot prosthesis is unable to provide the appropriate ankle posture during terminal swing phase to set up forefoot strike, and is similarly unable to absorb energy (without later releasing that energy) during the loading phase of stair descent.

SUMMARY

Embodiments of the invention concern apparatus and methods for stair ascent and descent control for powered lower limb devices. In a first embodiment, there is provided a method of operating a lower limb device including a powered knee joint and a powered ankle joint. The method includes configuring the lower limb device to a state of a finite state model for a current activity mode including a stair ascent mode. The method also includes, based on real-time sensor information for the lower limb device, transitioning the lower limb device from a current state to a subsequent state in the finite state model when a pre-defined criteria for transitioning to the subsequent state is met and repeating the transitioning until the current activity mode changes. In the method, the finite state model for the stair ascent mode includes a series of states defining at least one lifting state and at least one swing state, the at least one lifting state including a powered knee extension and a powered ankle push-off.

In the method, the series of states defining at least one lifting state include a powered knee straightening state and an ankle push off portion state, and the series of states defining the at least one swing state include a knee flexion state and a knee extension state. In the method, the transitioning between at least one lifting state and the swing phase is based on at least a measurement of load in the prosthesis.

The method can further include selecting the current activity mode to be the stair ascent mode when an estimate of an orientation with respect to gravity for a thigh associated with the powered knee joint indicates hip extension for a period of time. The method can also include selecting to exit the stair ascent mode when an estimate of an orientation with respect to gravity for a thigh associated with the powered knee joint fails to indicate an amount of hip flexion for a period of time. The method can also include selecting to change the current activity mode to or from the stair ascent mode based on a measurement of at least one of a stance time, a swing time, or a stride time.

In a second embodiment of the invention, there is also provided a method of operating a lower limb device including a powered knee joint and a powered ankle joint. The method includes configuring the lower limb device to a state in a finite state model for a current activity mode including a stair descent mode. The method also includes, based on real-time sensor information for the lower limb device, transitioning the lower limb device from a current state to a subsequent state in the finite state model when a pre-defined criteria for transitioning to the subsequent state is met and repeating the transitioning until the current activity mode changes. In the method, the finite state model for the stair descent mode includes a series of states defining at least one yielding state and at least one swing state, where the at least one swing state includes providing a powered plantarflexion of the powered ankle joint, and where the at least one yielding state includes providing a resistive and passive dorsiflexion of the powered ankle joint. In the method, the at least one yielding state can also include providing a resistive and passive flexion of the powered knee joint.

In the method, the series of states in the at least one yielding state includes an ankle dorsiflexion state and a knee flexion state, and where the series of states for the at least one swing state includes a knee flexion state and a knee extension state. Further, the transitioning between the at least one yielding state and the at least one swing state is based on at least a measurement of load in the lower limb prosthesis. Also, the transitioning between the at least one yielding state and the at least one swing state is based on at least a measure of ankle angle.

The method can further include selecting the current activity mode to be the stair descent mode when an estimate of the orientation of the user's thigh with respect to gravity indicates hip flexion for a period of time. Also, the method can further include selecting to exit the stair descent mode when an estimate of the orientation with respect to gravity for a thigh associated with the powered knee joint indicates the absence of hip flexion for a period of time. Additionally, the method can further include selecting to change the current activity mode to or from the stair descent mode based on a measurement of at least one of a stance time, a swing time, or a stride time.

In a third embodiment of the invention, there is provided a computer-readable medium, having stored thereon a plurality of instructions for causing a computing device to perform any of the methods described above.

In a fourth embodiment of the invention, there is provided a system for controlling a lower limb device including a powered knee joint and a powered ankle joint. The system includes at least one sensor for generating real-time sensor information for the lower limb device, and at least one processor communicatively coupled to the at least one sensor and to the lower limb device. The system also includes a computer-readable medium, having stored thereon instructions for causing the processor to perform any of the methods described above.

DETAILED DESCRIPTION

Figure 1A:
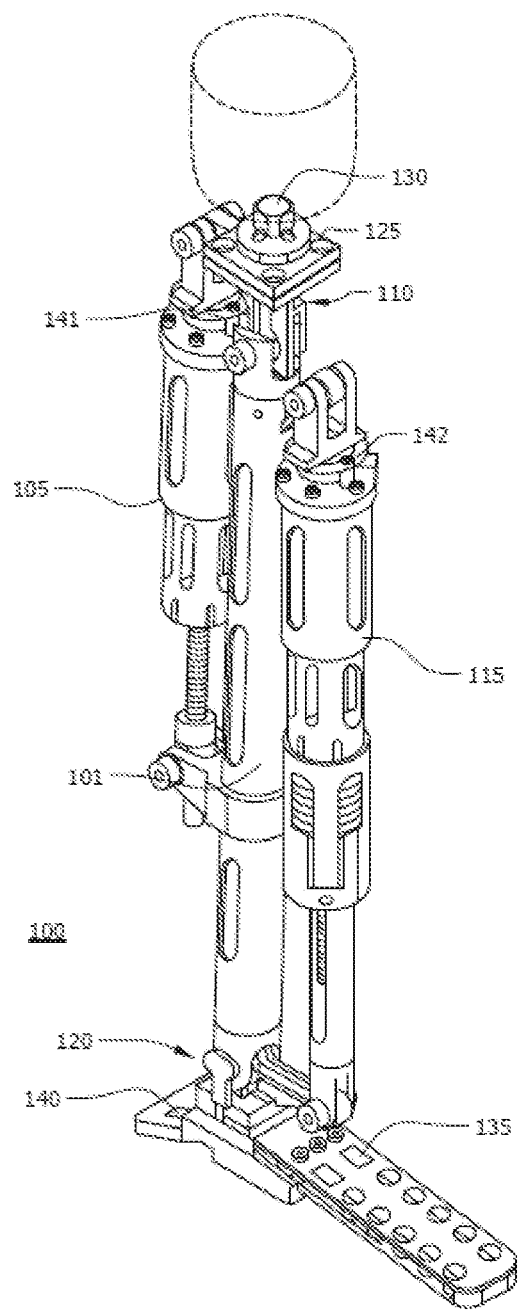
FIG. 1A is a view of a powered knee and ankle prosthesis, according to an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

In view of the limitations of existing lower limb prostheses, the various embodiments provide a new stair ascent and descent control system ("stair controller") for a powered knee and ankle prostheses. In the various embodiments, the stair controller can be configured to supplement an existing control system for a lower limb prosthesis. Specifically, ascent and descent can be controlled by providing activity-level controllers implemented in the form of a finite state machine (FSM). Each state within the FSM generates torque commands for the knee and ankle joints that ensure passivity within the state. Further, the states and transitions between the states are selected so as to provide a gait during ascent and descent that approximates the gait in an individual with healthy lower limbs.

Prior to discussing the stair ascent and descent, the disclosure first turns to FIGS. 1A-30 to describe various configurations for powered leg and ankle prostheses, including a controller, which can be modified to include a stair controller in accordance with the various embodiments of the invention.

Exemplary Prosthesis Configurations

A first design for a prosthesis for use in the various embodiments of the invention is shown in FIG. 1A through FIG. 6B. The prosthesis 100 comprises a prosthetic lower leg 101. Lower leg 101 can be coupled to a powered knee joint comprising a knee motor unit 105 coupled to a knee joint 110, and a powered ankle joint comprising an ankle motor 115 coupled to an ankle joint 120. A sagittal plane moment sensor 125 can be located between the prosthesis and the user to measure the moment, and in one embodiment is located immediately below the socket interface. In the embodiment shown, sensor 125 measures the sagittal plane moment, while separate sensors described below measure the ball of foot force and heel force with respect to the ground or other object the foot is pressed against. A load sensor 135 can be positioned at the ball of the foot, and a load sensor 140 can be positioned at the heel of the foot. However, in another embodiment (not shown) sensor 125 can measure the sagittal plane moment, the frontal plane moment and the axial force, such as provided by the three-axis socket load cell. This alternate embodiment can eliminate the need for sensor 135 and sensor 140.

Figure 4:
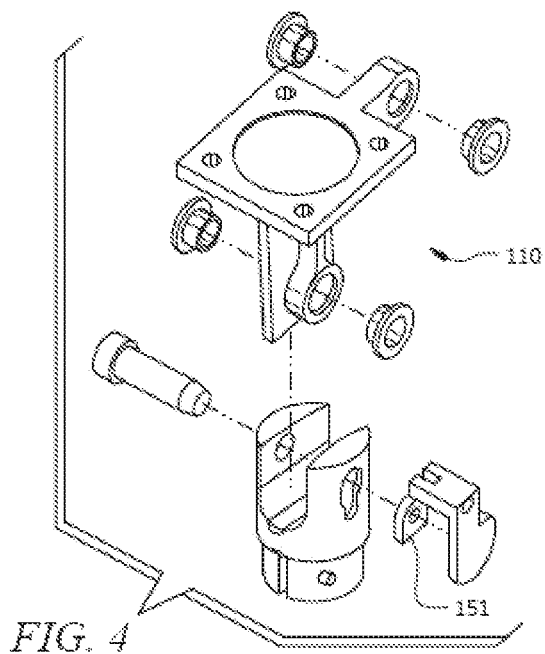
FIG. 4 is an exploded view of knee joint, according to an embodiment of the invention.
Figure 5:
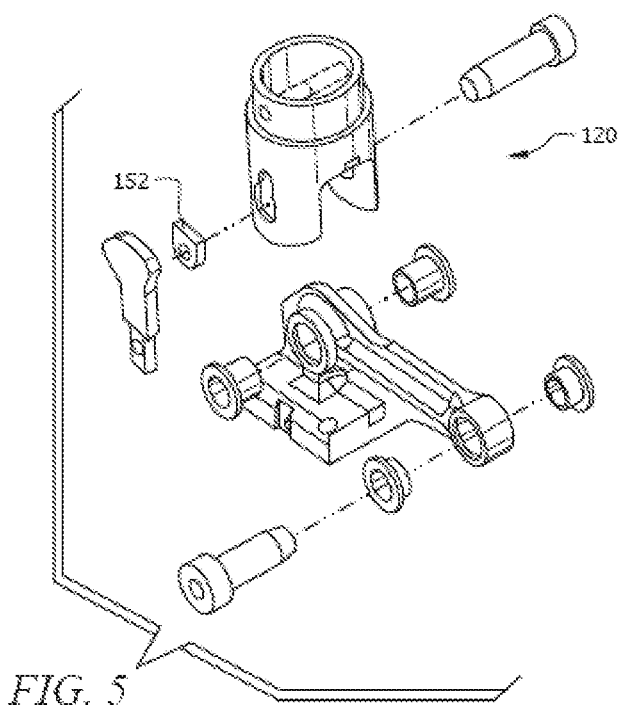
FIG. 5 is an exploded view of ankle joint, according to an embodiment of the invention.

Load sensors 141 and 142 are in series with each motor unit 105 and 115, respectively for motor unit force control. Position sensors 151 and 152 are provided at each joint 110 and 120 as shown in FIGS. 4 and 5 respectively. Position sensors 151 measure joint angle (θ as used below) and can be embodied as potentiometers. The computer/process controller, and power source (e.g. a battery such as a Li ion battery, and electrical connections in the case of an electrical power source are not shown to avoid obscuring aspects of the invention. Non-electrical power sources may also be used, such as pneumatic power, or non-battery electrical sources, such as hydrogen-based fuel cells.

Figure 1B:
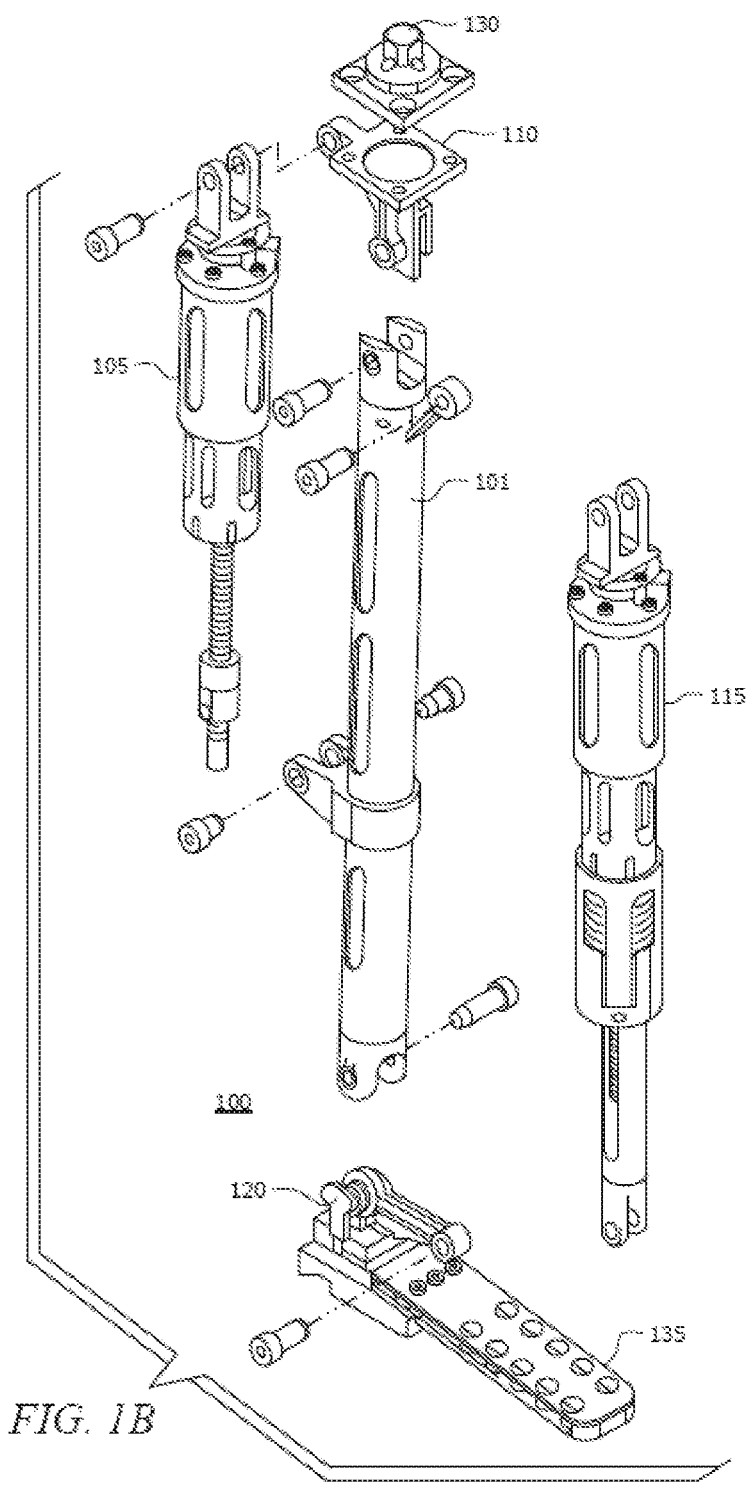
FIG. 1B is an exploded view of the powered knee and ankle prosthesis shown in FIG. 1A, according to an embodiment of the invention.

Prosthesis 100 is shown in an exploded view in FIG. 1B. Joints 110 and 120 are more clearly shown as compared to FIG. 1A.

Figure 2:
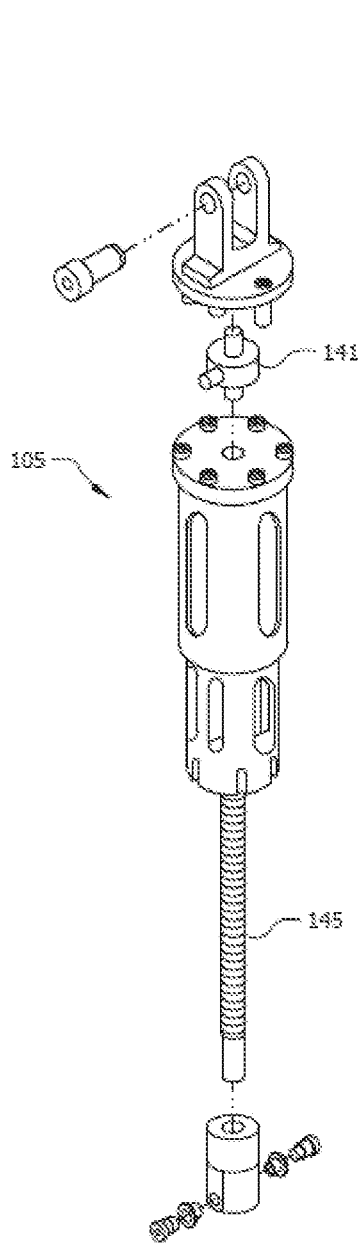
FIG. 2 is an exploded view of knee motor unit, according to an embodiment of the invention.

FIG. 2 is an exploded view of knee motor unit 105, according to an embodiment of the invention. Load sensor 141 is shown as a load cell (e.g. strain gauge). Load sensor 141 measures force and moments. The motor unit 105 comprises a motor-driven ball screw assembly which drives the knee joint through a slider-crank linkage comprising screw 145. Other motor drive assemblies may also generally be used.

Figure 3:
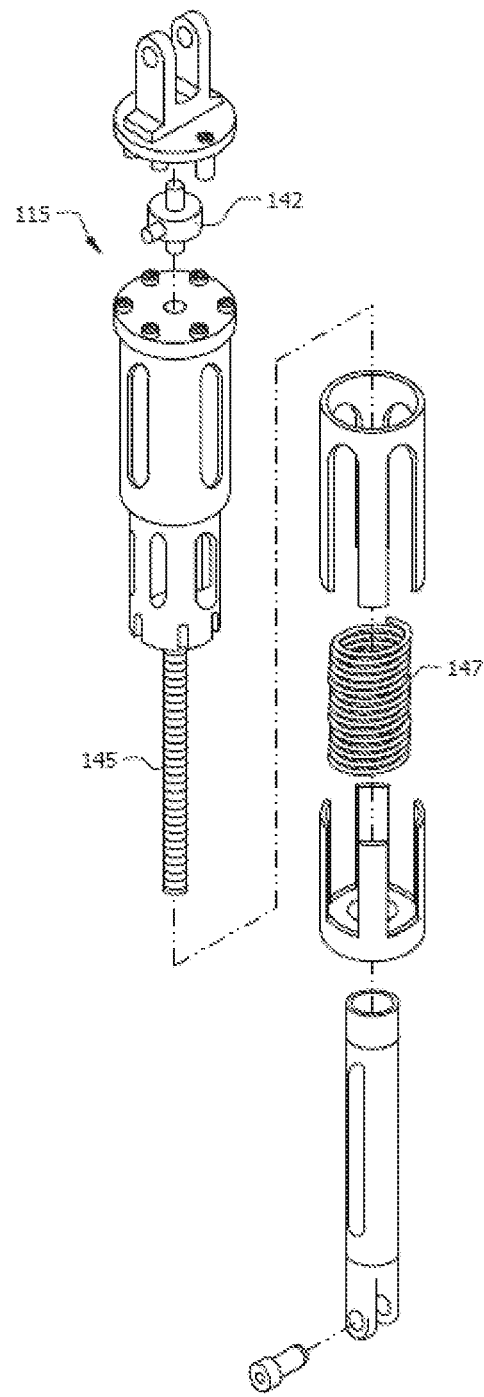
FIG. 3 is an exploded view of ankle motor unit, according to an embodiment of the invention.

FIG. 3 is an exploded view of ankle motor unit 115, according to an embodiment of the invention. Load sensor 142 is generally analogous to load sensor 141. The motor unit 115 comprises a motor-driven ball screw assembly which drives the ankle joint through a slider-crank linkage comprising screw 145. The ankle motor 115 includes a spring 147 positioned to provide power in parallel (thus being additive) with power provided by the motor unit 115. Spring 147 biases the motor unit's force output toward ankle plantarflexion, and supplements the power output provided by motor unit 115 during ankle push off.

FIG. 4 is an exploded view of knee joint 110, according to an embodiment of the invention. As described above, knee joint 110 includes position sensor 151 that can be embodied as a potentiometer for angle measurements of the knee joint 110.

FIG. 5 is an exploded view of ankle joint 120, according to an embodiment of the invention. As described above, ankle joint 120 includes position sensor 152 that can be embodied as a potentiometer for angle measurements of the ankle joint 120.

Figure 6A:
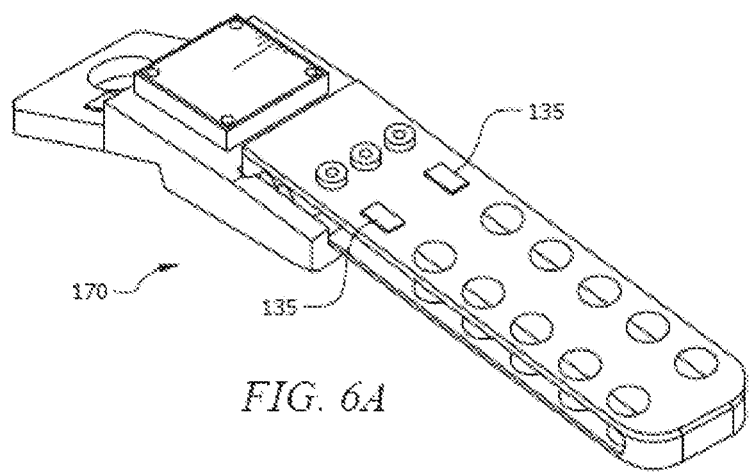
FIGS. 6A and B are views of a foot having toe and heel force sensing elements, according to an embodiment of the invention.
Figure 6B:
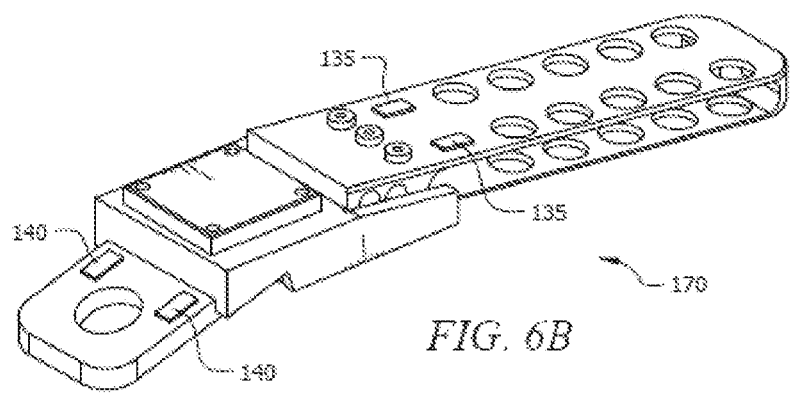

FIG. 6A is a view of a foot 170 having ball of foot sensors 135, according to an embodiment of the invention. Sensors 135 are provided to measure the ground reaction forces near the ball of the foot, such as when the foot strikes the ground. FIG. 6B is a view of a foot 170 having ball of foot sensors 135 and heel sensors 140, according to an embodiment of the invention. Sensors 140 are provided to measure the ground reaction forces on the heel of the foot when the foot 170 strikes the ground. Sensors 135 and 140 can be embodied as strain based sensors.

Unlike existing passive prostheses, the introduction of power into a prosthesis according to embodiments of the invention provides the ability for the device to also act, rather than simply react. As such, the development of a suitable controller and control methodology that provides for stable and reliable interaction between the user and prosthesis is provided herein. Control according to embodiments of the invention has been found to enable the user to interact with the prosthesis by leveraging its dynamics in a manner similar to normal gait, and also generates more stable and more predictable behavior.

Thus, rather than gather user intent from the joint angle measurements from the contralateral unaffected leg, embodiments of the invention infer commands from the user via the (ipsilateral) forces and moments of interaction between the user and prosthesis. Specifically, the user interacts with the prosthesis by imparting forces and moments from the residual limb to the prosthesis, all of which can be measured via suitable sensor(s), such as sensors 125, 140 and 141 described above which measures moments/forces. These forces and moments serve not only as a means of physical interaction, but also serve as an implicit communication channel between the user and device, with the user's intent encoded in the measurements. Inferring the user's intent from the measured forces and moments of interaction according to embodiments of the invention provides several advantages relative to the known echo approach.

In one embodiment of the invention the torque required at each joint during a single stride (i.e. a single period of gait) can be piecewise represented by a series of passive impedance functions. A regression analysis of gait data indicates that joint torques can be characterized by functions of joint angle (θ) and angular velocity by an impedance model, such as the following exemplary passive impedance function shown in equation 1 below:

$$T = k_1(\theta - \theta_e) + b^*\dot{\theta} \qquad (1)$$

where $k_1$, b, and the equilibrium joint angle $\theta_e$ are all constants that are generally generated empirically, and are constants for a given joint during a given internal phase (e.g. knee, internal phase 3). $k_1$ characterizes the linear stiffness. b is the linear damping coefficient, θ is the measured joint angle which can characterize the state of the prosthesis, $\theta_e$ is the equilibrium angle, $\dot{\theta}$ is the angular velocity of the joint, and τ is the joint torque. Given these constants, together with instantaneous sensor measurements for θ and, $\theta_e$ the torque (τ) at the joints (knee and ankle) can be determined.

Figure 7:
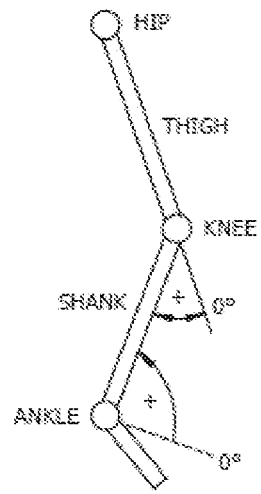
FIG. 7 shows the joint angle and torque convention used herein. Positive torque is defined in the direction of increasing angle.

Positive directions of the angle (θ) and torque (τ) as used herein are defined as shown in FIG. 7. If the coefficients b and $k_1$ are constrained to be positive, then the joints will each exponentially converge to a stable equilibrium at and $\theta=\theta_e$ and $\dot{\theta}=0$ within each internal phase. That is, within any given internal phase, the actuators are energetically passive (i.e. the joint will come to rest at a local equilibrium). While the unactuated prosthesis can be energetically passive, the behavior of one joint (knee or ankle) or the combined behavior of the knee and ankle joints, can be likewise passive, and thus will generally respond in a predictable manner.

Responsive to direct input from the user (e.g. a heel strike) to trigger a change in internal phase, power (torque) can be delivered from the power source (e.g. battery) to the prosthesis in the proper magnitude to provide the desired movement. Since the switching can be triggered by direct input from the user related to the current internal phase, the user maintains direct influence over the power applied to the prosthesis. If the user does not trigger the next internal phase (i.e. remains stationary) no net energy is delivered. That is, the prosthesis will generally cease to receive power from the power source for moving the joint, and will instead, due to the damped response, soon come to rest at the local equilibrium identified with the present internal phase.

As described above, the decomposition of joint behavior into passive segments requires the division of the gait cycle into a plurality of internal phases or "finite states" characterized by an impedance function and a set of constants for the impedance function, as dictated by their functions and the character of the piecewise segments of the impedance functions described above. The switching rules between internal phases should generally be well defined and measurable, and the number of phases should be sufficient to provide a substantially accurate representation of normal joint function. In one embodiment of the invention, the swing and stance phase of gait can constitute a minimal set of internal phases.

Figure 8:
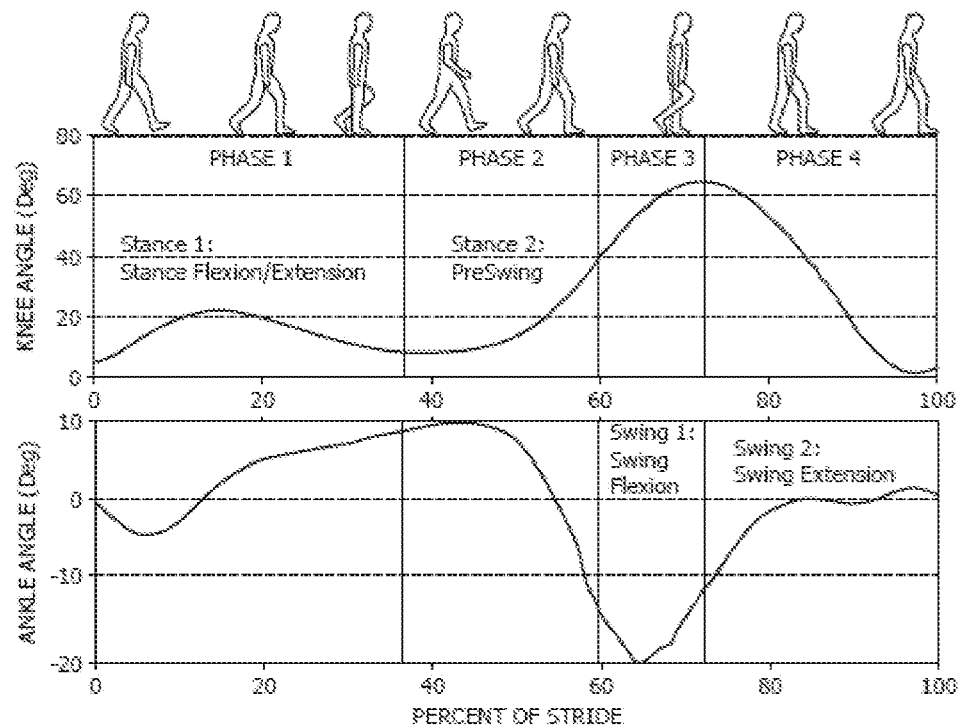
FIG. 8 shows the subdivision of normal walking into four internal phases showing the knee and ankle angles during the phases, according to an embodiment of the invention.
Figure 16:
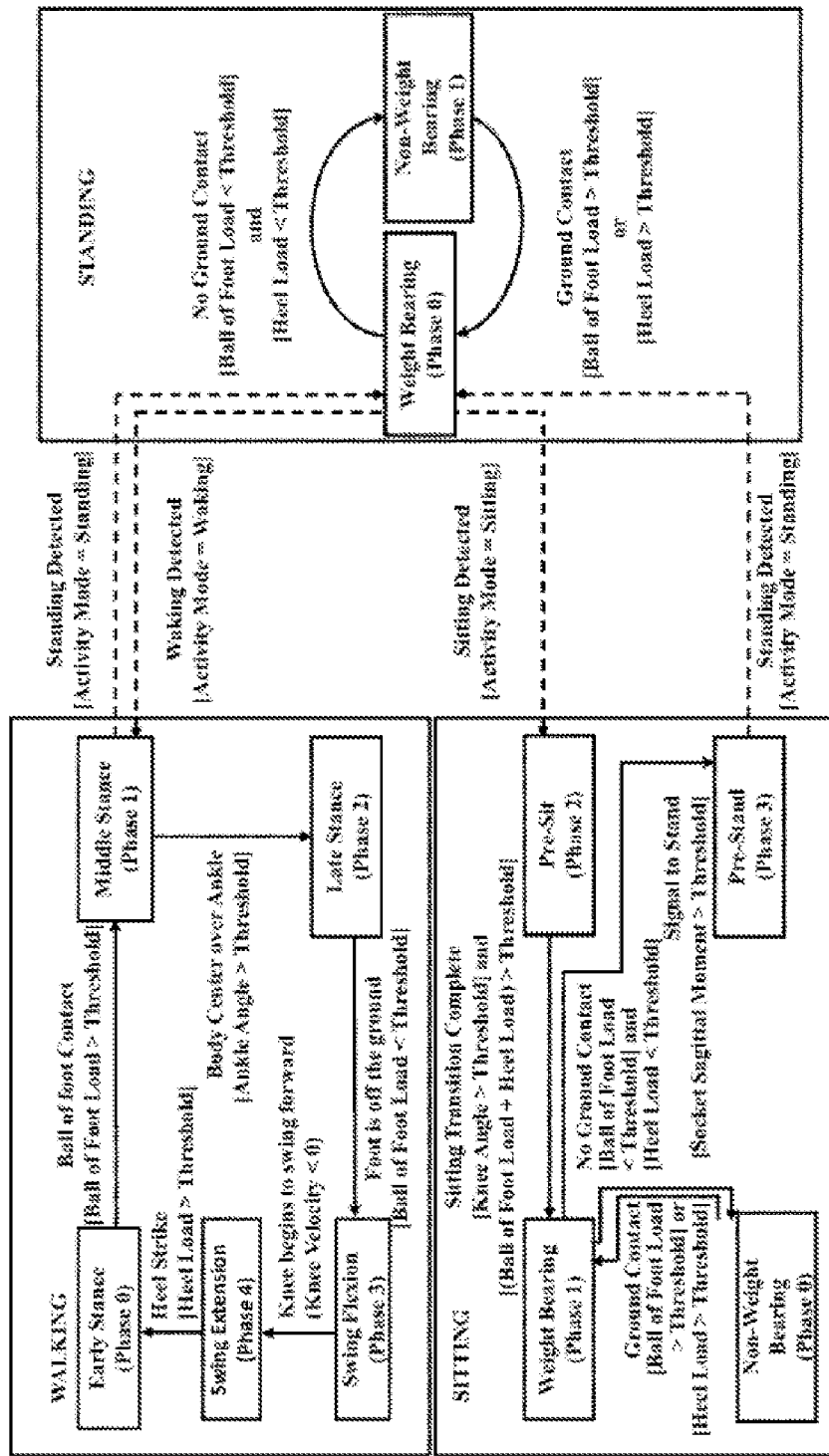
FIG. 16 is a control state chart for the three activity modes corresponding to walking, standing, and sitting, and for the internal phases and their corresponding transitions within each activity mode.

Based on least-squares regression fitting of Equation 1 to empirical gait data, the present Inventors determined that such fits were improved significantly by further dividing the two modes of swing and stance each into two additional internal phases to realize four phases, as shown in FIG. 8. A fifth internal phase can also be added, as illustrated in FIG. 16. The angle (θ) of the prosthetic knee (above) and ankle joint (below) can be provided during each internal phase as a function of the % of the stride. Angle values shown can be used as threshold values to trigger phase changes as described below relative to FIG. 9. As clear to one having ordinary skill in the art, the number of phases can be other than two or four.

Figure 9:
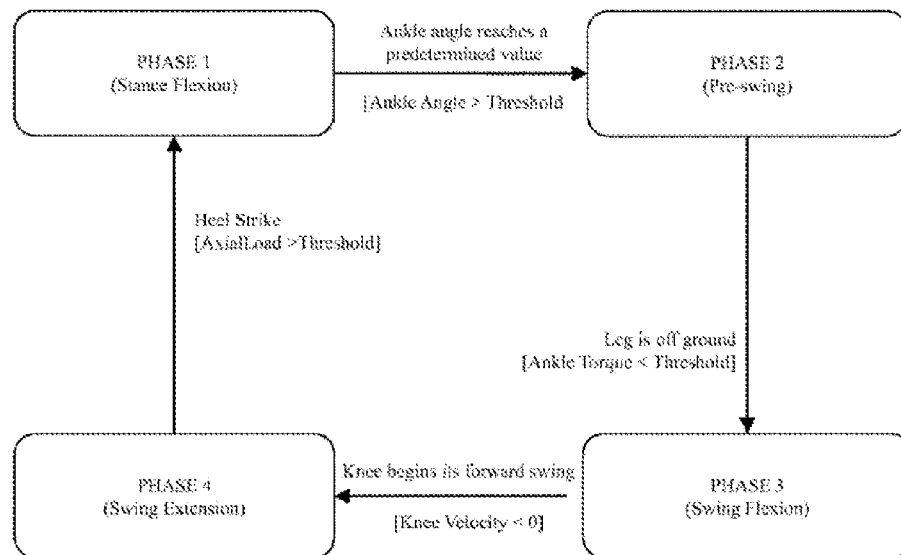
FIG. 9 shows a finite-state model of normal walking, according to an embodiment of the invention. Each box represents a different internal phase and the transition conditions between the internal phases are specified.

FIG. 9 shows exemplary switching rules between internal phases for walking. FIG. 16 shows another set exemplary switching rules, for walking, standing, and sitting activity modes. As described above, if the user does not initiate actions that trigger the next phase (e.g. based on the switching rules), the prosthesis will cease to receive power and will come to rest at the local equilibrium identified with the present phase. For example, switching can be based on the ankle angle>a threshold value (mode 1 to mode 2), or ankle torque<threshold) (mode 2 to mode 3), the angle or torque measurements provided by on board sensors as described above.

Phase 1 shown in FIG. 8 begins with a heel strike by the user (which can be sensed by the heel force sensor), upon which the knee immediately begins to flex so as to provide impact absorption and begin loading, while the ankle simultaneously plantarflexes to reach a flat foot state. Both knee and ankle joints have relatively high stiffness (and can be accounted for by k1 in equation 1) during this phase to prevent buckling and allow for appropriate stance knee flexion, because phase 1 comprises most of the weight bearing functionality. Phase 2 is the push-off phase and begins as the ankle dorsiflexes beyond a given angle (i.e. user's center of mass lies forward of stance foot). The knee stiffness decreases in this mode to allow knee flexion while the ankle provides a plantarflexive torque for push-off. Phase 3 begins as the foot leaves the ground as detected by the ankle torque load cell and lasts until the knee reaches maximum flexion. Mode 4 is active during the extension of the knee joint (i.e. as the lower leg swings forward), which begins as the knee velocity becomes negative and ends at heel strike (e.g. as determined by the heel force sensor).

In both of the swing phases (Phases 3 and 4), the ankle torque can be small and can be represented in the controller as a (relatively) weak spring regulated to a neutral position. The knee can be primarily treated as a damper in both swing phases.

Figure 10:
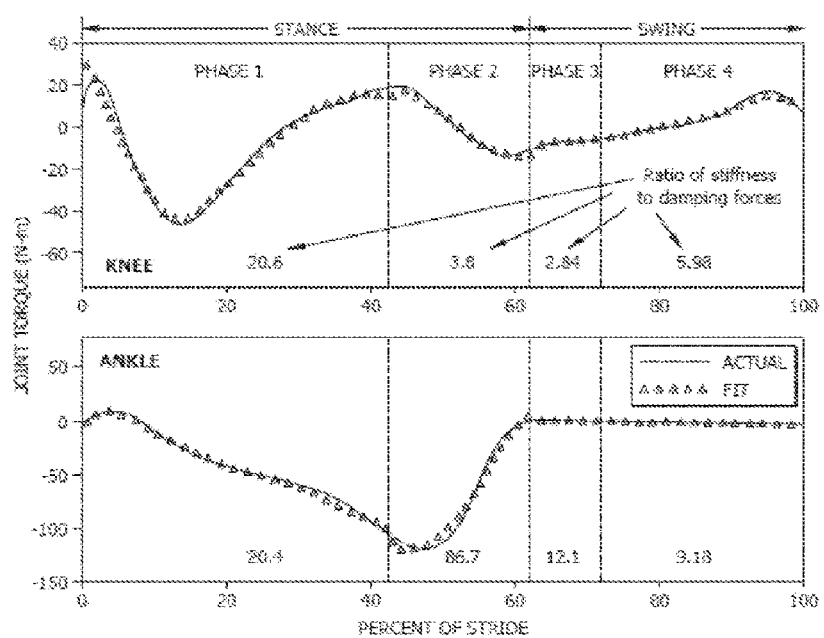
FIG. 10 shows piecewise fitting of knee and ankle torques during normal speed level walk scaled for a 75 kg adult to a non-linear spring-damper impedance model.

Impedance modeling of joint torques was preliminarily validated by utilizing the gait data from a healthy 75 kg subject, as derived from body-mass normalized data. Incorporating the four internal phases described above, along with the motion and torque data for each joint, a constrained least-squares optimization was conducted to generate a set of parameters $k_1$, b and $\theta_e$ for each phase for each joint for use in Equation 1. The resulting parameter set can be fit to joint torques and is shown graphically in FIG. 10. FIG. 10 shows piecewise fitting of knee and ankle torques during normal speed level walk scaled for a 75 kg adult to a non-linear spring-damper impedance model. The numbers shown in each phase represent the mean ratio of the stiffness forces to damping forces predicted by the fit. The vertical lines represent the segmentation of a gait stride into four distinct phases. The fit shown in FIG. 10 clearly indicates that normal joint function can be represented by the use of piecewise passive functions.

Controllers according to embodiments of the invention generally comprise an underlying gait controller (intra-modal controller). An optional supervisory gait controller (also called intent recognizer) can also be provided. Both controllers generally utilize measured information. This information generally comprises user and ground interaction forces (F) and moments/torques ($\tau$), joint angles and angular velocities from on-board sensors, and can be used to extract real-time input from the user. The gait control component utilizes the sensed instantaneous nature of the user input (i.e., moments and forces) to control the behavior of the leg within a given activity mode, such as standing, walking, or stair climbing.

Figure 11:
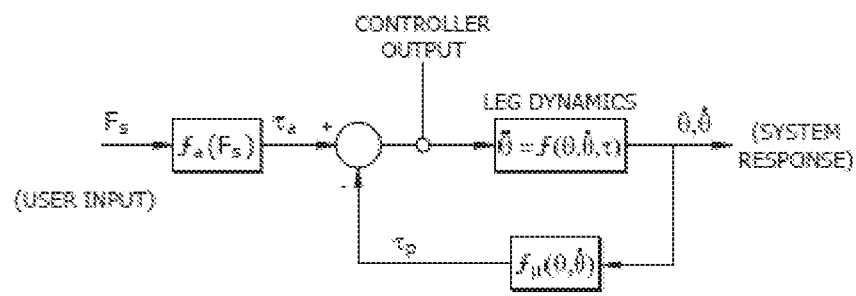
FIG. 11 is a diagram for an active/passive decomposition based control of the powered knee and ankle prosthesis, according to an embodiment of the invention.
Figure 12:
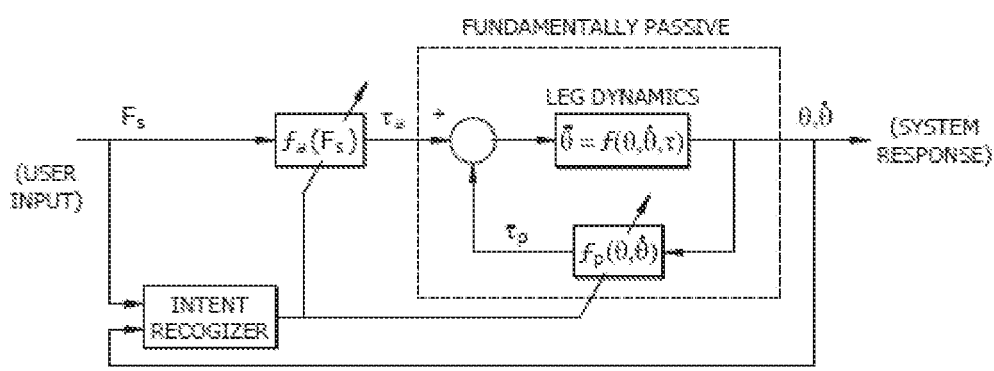
FIG. 12 is a diagram for a general form of active-passive decomposition control including intent recognition that provides supervisory modulation, according to an embodiment of the invention.

Two exemplary approaches to intra-modal impedance generation are described below. The first approach is shown in FIG. 11 and represents a general form of active-passive decomposition-based intra-mode control. The second embodiment shown in FIG. 12 includes the control structure shown in FIG. 11 but adds a supervisory intent recognizing controller to modulate the intra-modal control based on inputs from an intent recognition module. As shown in FIGS. 11 and 12, $F_s$ is the force the user of the prosthesis is applying, such as a heel force in the case of a heel strike, $\tau$ represents joint torque, and $\theta$ represent joint angles. $\tau_a$ represents the active component of joint torque which is roughly proportional to the input force, and $\tau_p$ represents the passive component of torque. The active joint torque $\tau_a$ is thus the total joint torque $\tau$ minus the passive joint torque, $\tau p$. Derivatives are shown using the dot convention, with one dot being the first derivative (e.g., $\dot{\theta}$ being angular velocity) and two dots representing the second derivative.

In the embodiment of the intra-modal controller shown in FIG. 11, the behavior of the prosthesis can be decomposed into a passive component and an active control component. The active control component is an algebraic function of the user's real-time input $F_s$ (i.e., sensed socket-prosthesis interface forces and moments and sensed ground reaction forces). The controller output is shown as the active torque ($\tau_a$) minus the passive torque $\tau_p$. The controller output $\tau_a$–$\tau_p$ applied to the prosthetic leg based on dynamics of the leg responds via $\theta$ and $\dot{\theta}$. The system response, $\theta$ and $\dot{\theta}$, is fed back to the controller.

Power applied to the prosthesis can be thus commanded directly by the user through measured interface forces and moments initiated by user movements. In the absence of these commands from the user, $F_s$=0, $\tau_s$=0 and the prosthesis fundamentally (by virtue of the control structure) cannot generate power, and thus only exhibits controlled passive behavior. Due to the decomposition of energetic behaviors inherent in this control structure, the prosthesis under it's own control can be generally stable and passive. Unlike known echo control approaches, the input can be real-time, based only on the affected leg, and thus the approach can be equally applicable to bilateral and unilateral amputees and can reflect the instantaneous intent of the user. Additionally, unlike echo control that is based on servocontrol, the prosthesis will exhibit a natural impedance to the user that should feel more like a natural limb. These combined features should result in an active prosthesis that will feel inasmuch as possible like a natural extension of the user. The structure and properties of both the gait controller and intent recognizer are described below.

As described above, since gait is largely a periodic activity, joint behavior can be functionally decomposed over a period by decomposing the joint torque into a passive component and an active component. The passive component can comprise a function of angle (i.e., single-valued and odd), and a function of angular velocity passive (i.e., single-valued and odd), such as equation 1 described above. The active component can be a function of the user input (i.e., socket interface forces). Given a set of data that characterizes a nominal period of joint behavior, the passive component can be first extracted from the whole, since the passive behavior is a subset of the whole (i.e., the passive component consists of single-valued and odd functions, while the active has no restrictions in form). The passive component can be extracted by utilizing a least squares minimization to fit a generalized singled-valued odd function of angle and angular velocity to the torque. Once the passive component is extracted, the residual torque (i.e., the portion that is not extracted as a passive component), can be constructed as an algebraic function of the sensed socket interface and ground reaction forces (i.e., the direct-acting user input) by incorporating a similar candidate function, but not restricted to be of passive form. Finally, superimposing the passive and active components provides a decomposed functional approximation of the original period joint torque.

In the embodiment of the intra-modal controller shown in FIG. 12, a supervisory intent recognizer can be added that utilizes the same sensed user inputs (i.e., moments and forces) as the intra-modal/gait controller, but extracts the user's intent based on the characteristic shape of the user input(s) and system response (e.g. F, $\theta$, $\theta$-dot). Based on the extracted intent, the supervisory intent recognizer modulates the behavior of the underlying gait controller to smoothly transition behavior within a gait (e.g., speed and slope accommodation) and between gaits (e.g., level walk to stair ascent), thus offering a unified control structure within and across all gaits.

Gait intent recognition can be a real-time pattern recognition or signal classification problem. The signal in this case is generally the combination of socket interface forces Fs and the dynamic state of the prosthesis, which in one embodiment can be a vector of the knee and ankle angles $\theta$ for a powered leg prosthesis according to an embodiment of the invention. A variety of methods exist for pattern recognition and signal classification including nearest neighbor algorithms, neural networks, fuzzy classifiers, linear discriminant analysis, and genetic algorithms.

Figures 13A, 13B:
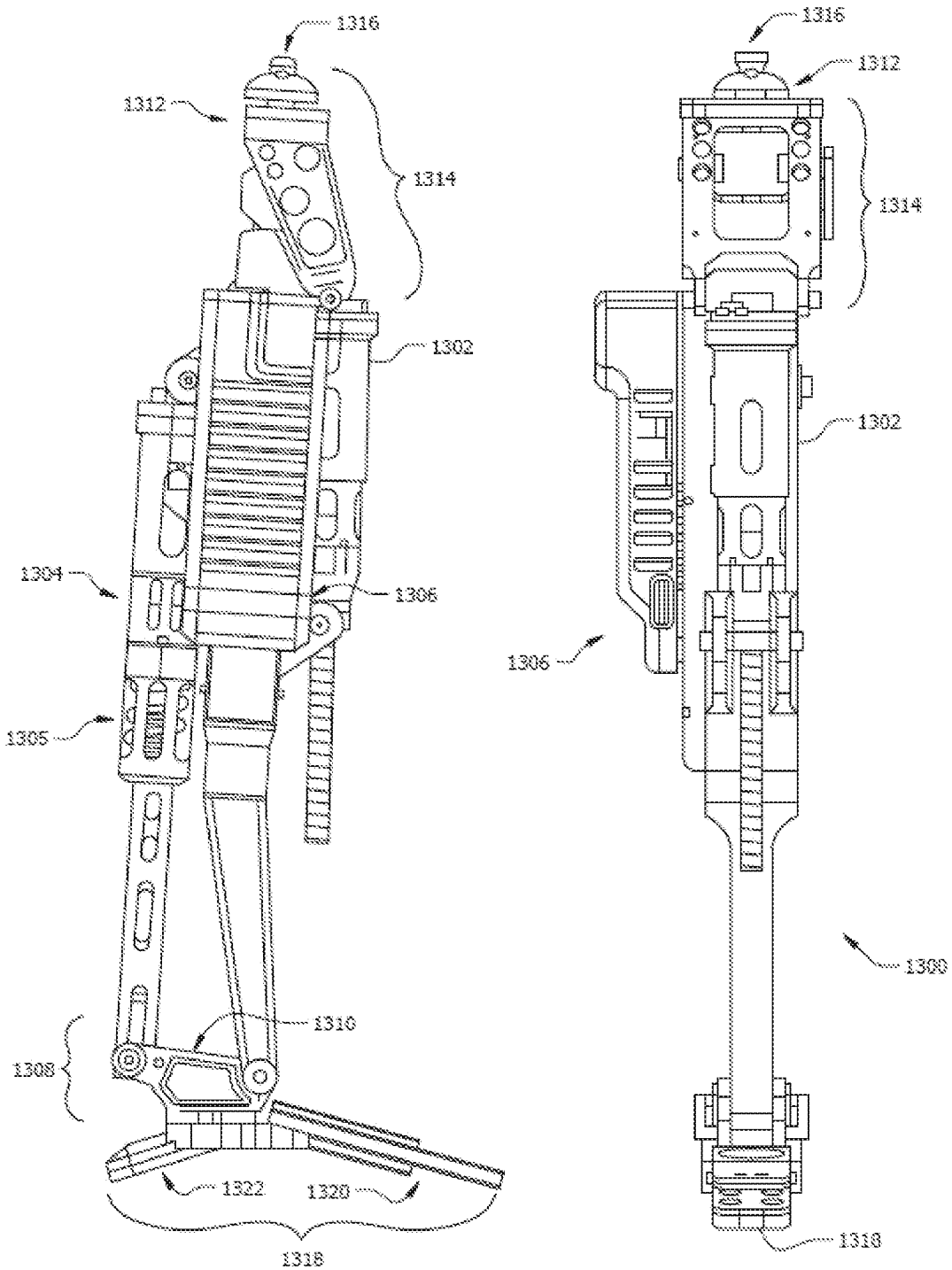
FIG. 13A is a side view of powered knee and ankle prosthesis, according to another embodiment of the invention.
FIG. 13B is a front view of powered knee and ankle prosthesis of FIG. 13A.
Figure 14A:
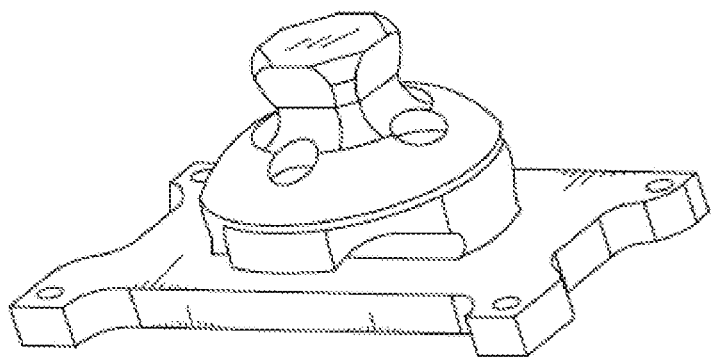
FIGS. 14A and 14B show perspective and bottom views of an exemplary sagittal moment load cell suitable for use in the various embodiments of the invention.
Figure 14B:
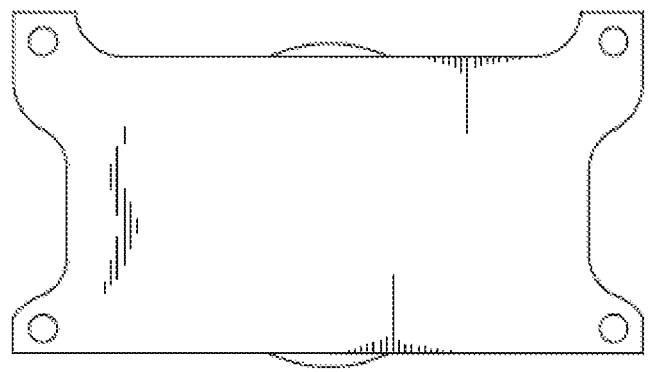
Figure 15:
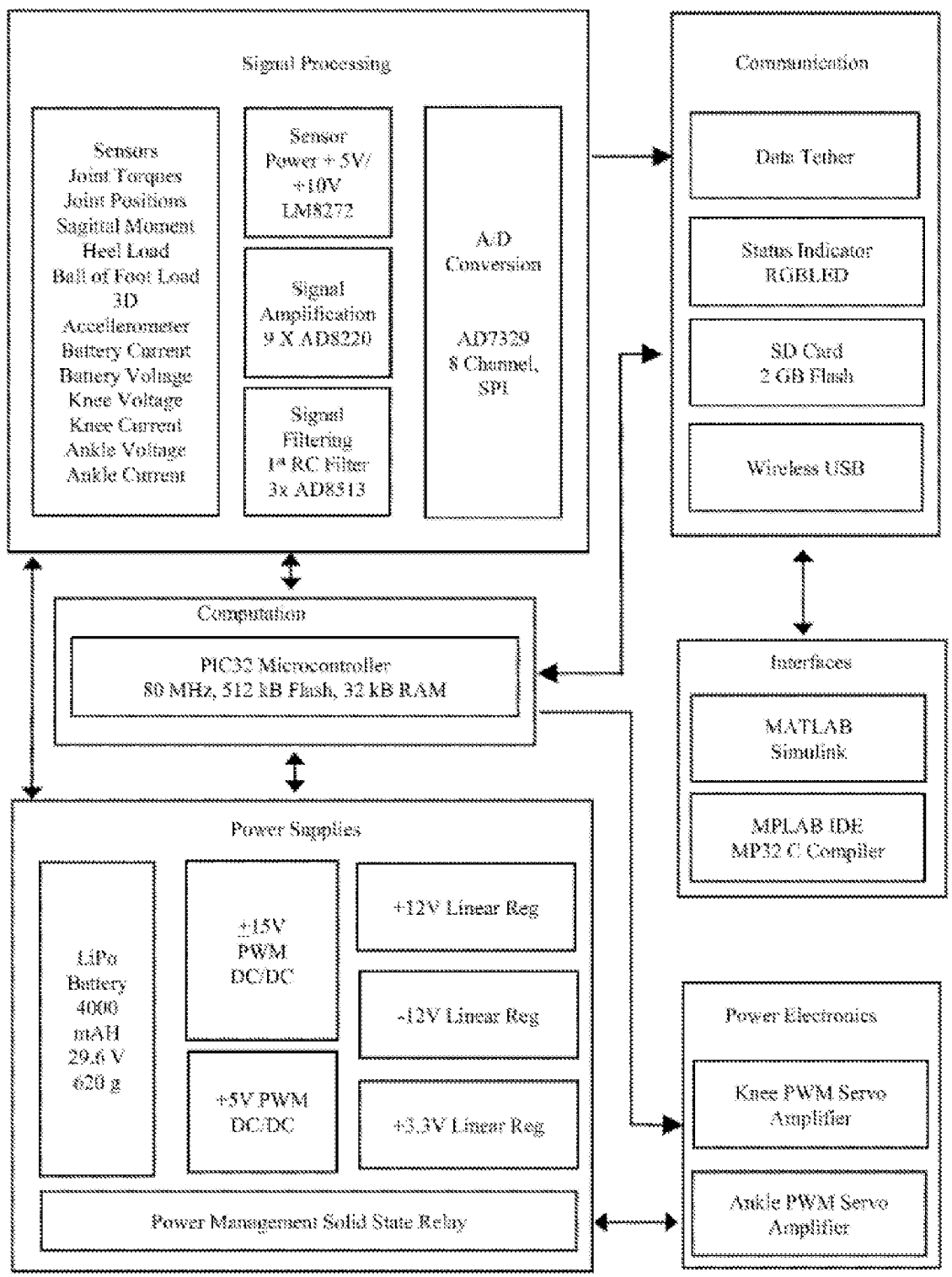
FIG. 15 is a block diagram of an exemplary embedded microcontroller in accordance with an embodiment of the invention.

As described above, embodiments of the invention include a number of sensors for providing signals for adjusting operation of a leg and ankle prosthesis. A description of one exemplary arrangement of sensors can be described below with respect to FIGS. 13A, 13B, 14A, and 14B. FIG. 13A is a side view of powered knee and ankle prosthesis 1300, according to another embodiment of the invention. FIG. 13B is a front view of powered knee and ankle prosthesis of FIG. 13A. FIGS. 14A and 14B show perspective and bottom views of an exemplary sagittal moment load cell suitable for use in the various embodiments of the invention.

Each joint actuation unit, such as knee actuation unit 1302 and ankle actuation unit 1304 in FIG. 13A, can include a uniaxial load cell positioned in series with the actuation unit for closed loop force control. Both the knee and ankle joints can incorporate integrated potentiometers for joint angle position. The ankle actuation unit can include a spring 1305, as described above with respect to FIGS. 1A-4. One 3-axis accelerometer can be located on the embedded system 1306 and a second one can be located below the ankle joint 1308 on the ankle pivot member 1310. A strain based sagittal plane moment sensor 1312, such as sensor 1400 shown in FIGS. 14A and 14B, can located between the knee joint 1314 and the socket connector 1316, which measures the moment between a socket and the prosthesis. In the various embodiments of the invention, a sagittal plane moment sensor can be designed to have a low profile in order to accommodate longer residual limbs. The sensor can incorporate a full bridge of semiconductor strain gages which measure the strains generated by the sagittal plane moment. In one embodiment of the invention, the sagittal plane moment sensor was calibrated for a measurement range of 100 Nm. A custom foot 1318 can designed to measure the ground reaction force components at the ball 1320 of the foot and heel 1322. The foot can include of heel and ball of foot beams, rigidly attached to a central fixture and arranged as cantilever beams with an arch that allows for the load to be localized at the heel and ball of the foot, respectively. Each heel and ball of foot beam can also incorporate[[s]] a full bridge of semiconductor strain gages that measure the strains resulting from the respective ground contact forces. In one embodiment of the invention, the heel and ball of foot load sensors were calibrated for a measurement range of 1000 N. In addition, incorporating the ground reaction load cell into the structure of a custom foot can eliminate the added weight of a separate load cell, and also enables separate measurement of the heel and ball of foot load. The prosthetic foot can be designed to be housed in a soft prosthetic foot shell (not shown).

The powered prostheses described above contain an embedded microcontroller that allows for either tethered or untethered operation. An exemplary embedded microcontroller system 1500 is shown in the block diagram in FIG. 15. The embedded system 1500 consists of signal processing, power supply, power electronics, communications and computation modules. The system can be powered by a lithium polymer battery with 29.6 V. The signal electronics require +/−12 V and +3.3 V, which are provided via linear regulators to maintain low noise levels. For efficiency, the battery voltage can be reduced by PWM switching amplifiers to +/−15 V and +5 V prior to using the linear regulators. The power can be disconnected via a microcontroller that controls a solid state relay. The power status can be indicated by LED status indicators controlled also by the microcontroller.

The analog sensor signals acquired by the embedded system include the prosthesis sensors signals (five strain gage signals and two potentiometer signals), analog reference signals from the laptop computer used for tethered operation, and signals measured on the board including battery current and voltage, knee and ankle servo amplifier currents and two 3-axis accelerometers. The prosthesis sensor signals are conditioned using input instrumentation amplifiers. The battery, knee motor and ankle motor currents are measured by current sense resistors and current sensing amplifiers. The signals are filtered with a first-order RC filter and buffered with high slew rate operational amplifiers before the analog to digital conversion stage. Analog to digital conversion can be accomplished by two 8-channel analog to digital convertors. The analog to digital conversion data can be transferred to the microcontroller via serial peripheral interface (SPI) bus.

The main computational element of the embedded system can be a 32-bit microcontroller. In the untethered operation state, the microcontroller performs the servo and activity controllers of the prosthesis and data logging at each sample time. In addition to untethered operation, the prosthesis can also be controlled via a tether by a laptop computer running MATLAB Simulink RealTime Workshop. In the tethered operation state, the microcontroller drives the servo amplifiers based on analog reference signals from the laptop computer. A memory card can be used for logging time-stamped data acquired from the sensors and recording internal controller information. The memory chip can be interfaced to the computer via wireless USB protocol. The microcontroller sends PWM reference signals to two four quadrant brushless DC motor drivers with regenerative capabilities in the second and forth quadrants of the velocity/torque curve.

Figure 17:
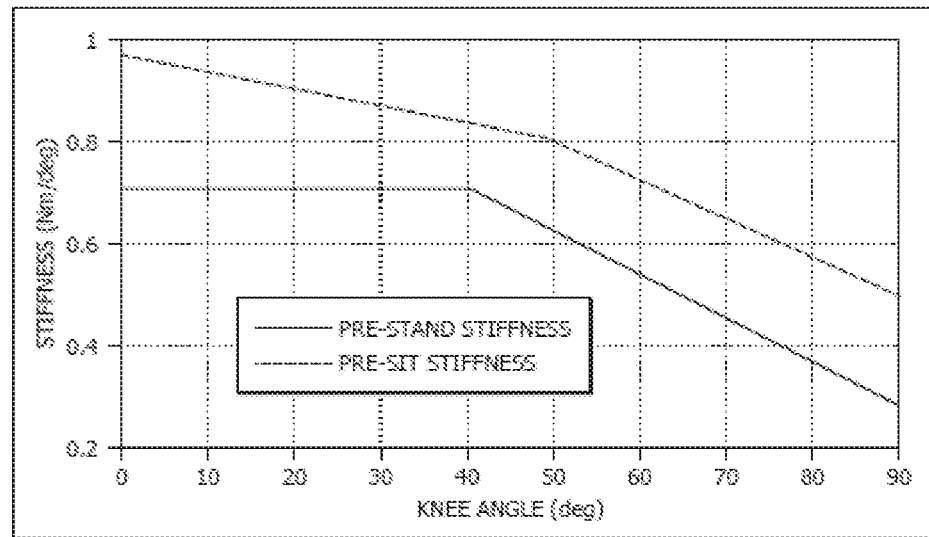
FIG. 17 shows knee angle modulated knee stiffness during pre-stand (solid line) and pre-sit (dashed line) phases.

As noted above with respect to FIG. 9, additional controls can be provided for operating the prosthesis when going from a sitting to a standing position or vice versa. This can be implemented via the use of a sitting mode controller implemented in the microcontroller. Operation of the sitting mode controller consists of four phases that are outlined in the general control state chart shown in FIG. 16. As shown in FIG. 16, two phases are primary sitting phases, weight bearing and non-weight bearing. The other two phases encompass the transition phases, pre-stand and pre-sit, for standing up and sitting down, respectively. Weight bearing and non-weight bearing are the primary sitting phases that switch the knee and ankle joints between high and low impedances, respectively. The transition phases, pre-stand and pre-sit, modulate the stiffness of the knee as a function of knee angle, as shown in FIG. 17, to assist the user in standing up and sitting down. FIG. 17 shows knee angle modulated knee stiffness during pre-stand (solid line) and pre-sit (dashed line) phases.

The modulation allows for smoother transitions near the seated position. The ankle joint can be slightly dorsiflexed with moderate stiffness during the standing up and sitting down phases. Switching between the four sitting phases occurs when sensor thresholds are exceeded, as depicted FIG. 16. The parameters of the impedance based controllers are tuned using a combination of feedback from the user and joint angle, torque and power data from the prosthesis.

In the various embodiments of the invention, actuation for a prosthesis can be provided by two motor-driven ball screw assemblies that drive the knee and ankle joints, respectively, through a slider-crank linkage. The prosthesis can be capable of 120° of flexion at the knee and 45° of planterflexion and 20° of dorsiflexion at the ankle. In one embodiment, each actuation unit consists of a DC motor (such as a Maxon EC30 Powermax) connected to a 12 mm diameter 20 ball screw with 2 mm pitch, via helical shaft couplings. An exemplary ankle actuation unit additionally incorporates a 302 stainless steel spring (51 mm free length and 35 mm outer diameter), with 3 active coils and a stiffness of 385 N/cm in parallel with the ball screw.

Figure 18:
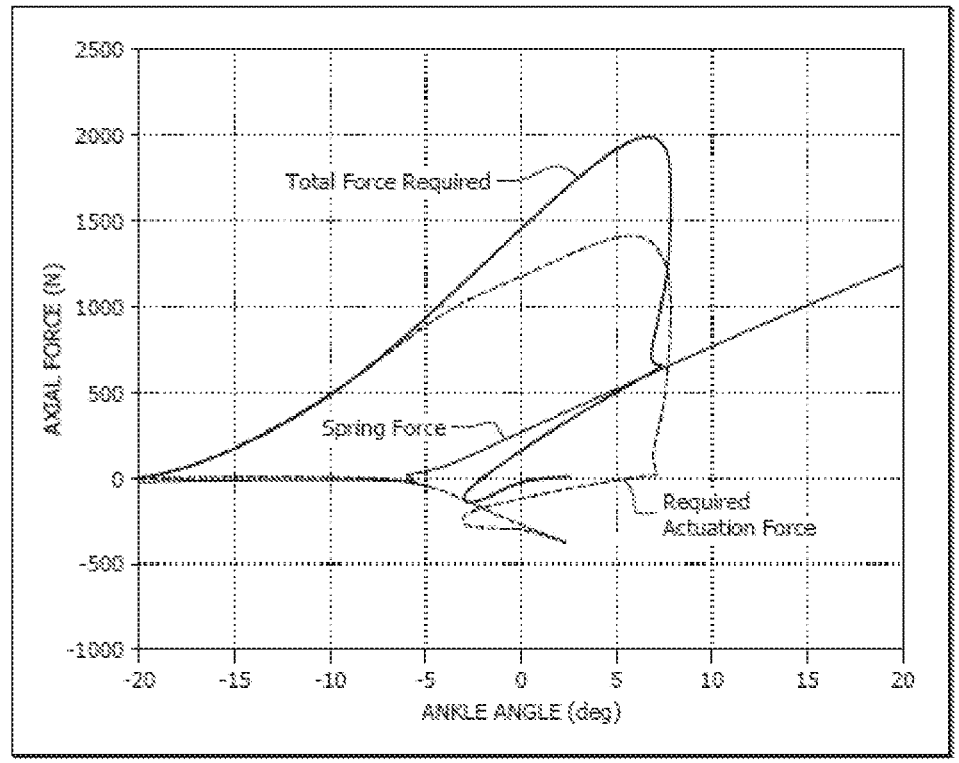
FIG. 18 is a plot of axial actuation unit force versus ankle angle.

As described above with respect to FIGS. 1A-4, the purpose of the spring can be to bias the motor's axial force output toward ankle plantarflexion, and to supplement power output during ankle push off. The stiffness of the spring can be maximized to allow for peak force output without limiting the range of motion at the ankle. The resulting axial actuation unit's force versus ankle angle plot can be shown in FIG. 18. FIG. 18 is a plot if axial force as a function of ankle angle illustrating spring force, actuator force and total force. FIG. 18 graphically demonstrates for fast walking the reduction in linear force output supplied by the motor at the ankle through the addition of the spring. Note that the compression spring does not engage until approximately five degrees of ankle plantarflexion. Each actuation unit can include a uniaxial load cell (such as Measurement Specialties ELPF-500L), positioned in series with the actuation unit for closed loop force control of the motor/ballscrew unit. Both the knee and ankle joints can incorporate bronze bearings and, for joint angle measurement, integrated precision potentiometers (such as an ALPS RDC503013). A strain based sagittal plane moment sensor, as previously described with respect to FIGS. 14A and 14B can be located between the knee joint and the socket connector, which measures the moment between the socket and prosthesis. The ankle joint connects to a foot, which incorporates strain gages to measure the ground reaction forces on the ball of the foot and on the heel. The central hollow structure houses a lithium-polymer battery and provides an attachment point for the embedded system hardware. To better fit with an anthropomorphic envelope, the ankle joint can be placed slightly anterior to the centerline of the central structure. This gives the prosthesis the illusion of flexion when the amputee can be standing vertically with the knee fully extended.

The length of the shank segment can be varied by changing the length of three components; the lower shank extension, the spring pull-down, and the coupler between the ball nut and ankle. Additional adjustability can be provided by the pyramid connector that can be integrated into the sagittal moment load cell for coupling the prosthesis to the socket (as is standard in commercial transfemoral prostheses).

Passive joint torque, $\tau_p$, can be defined as the part of the joint torque, $\tau$, which can be represented using spring and dashpot constitutional relationships (passive impedance behavior). The system can only store or dissipate energy due to this component. The active part can be interpreted as the part which supplies energy to the system and the active joint torque can be defined as $\tau_a = \tau - \tau_p$. This active part can be represented as an algebraic function of the user input via the mechanical sensory interface (i.e. socket interface forces and torques).

Figure 19:
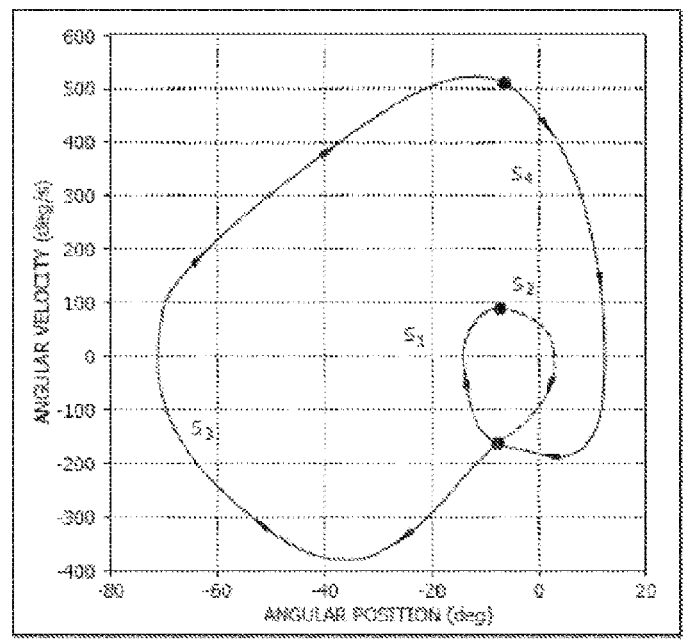
FIG. 19 shows a normal speed walking phase portrait of the knee joint and four stride segments.

Gait is considered a mainly periodic phenomena with the periods corresponding to the strides. Hence, the decomposition of a stride will give the required active and passive torque mappings for a specific activity mode. In general, the joint behavior exhibits varying active and passive behavior in each stride. Therefore, segmenting of the stride in several parts can be necessary. In this case, decomposition of the torque over the entire stride period requires the decomposition of the different segments and piecewise reconstruction of the entire segment period. In order to maintain passive behavior, however, the segments cannot be divided arbitrarily, but rather can only be segmented when the stored energy in the passive elastic element is zero. This requires that the phase space can only be segmented when the joint angle begins and ends at the same value. FIG. 19 shows the phase portrait of normal speed walking and the four different stride segments, $S_1$, $S_2$, $S_3$, and $S_4$. Thus, the entire decomposition process consists of first appropriate segmentation of the joint behavior, followed by the decomposition of each segment into its fundamental passive and active components.

Figure 20:
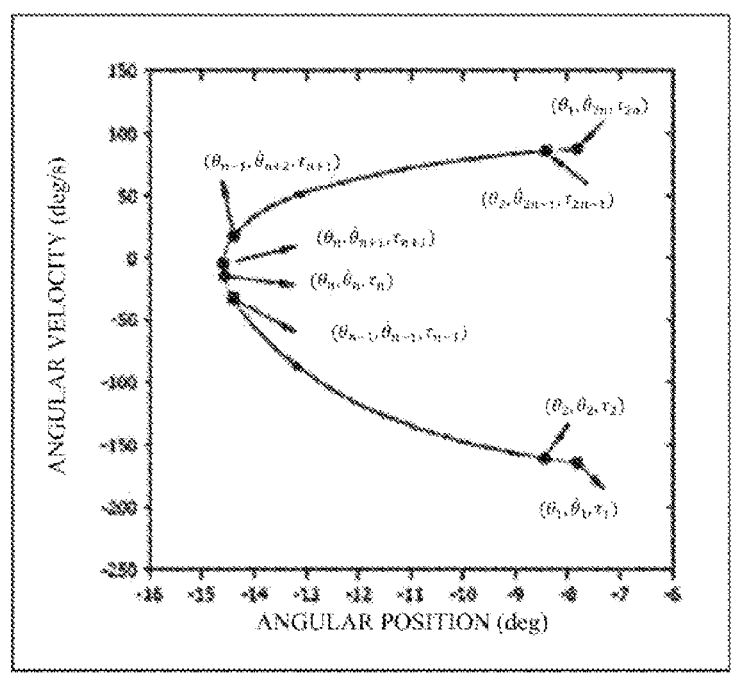
FIG. 20 shows the selection of indexing data samples during a first segment of a walking stride.

The decomposition of each segment shown in FIG. 19 can be converted to an optimization problem. In each segment of the stride, 2n data points are selected by sampling the angular position in equal intervals between its minimum and maximum and selecting the corresponding positive and negative angular velocities. In this work, the number of angular position samples for each segment, n can be set to be 100. The constrained least squares optimization problem given in Equation 2 below can be constructed and solved.

$$\min_x \frac{1}{2}\|Cx - d\|_2^2 \text{ s.t. } 0 \le x \tag{2}$$

where C, x and d are defined in Equations 3, 4, and 5 below, respectively. The indexing of the joint angular position, angular velocity and moment samples are explained via the sketch in FIG. 20. FIG. 20 shows a selection and indexing of data samples from a first segment.

$$C_{4n \times 3n} = [C_1 C_2 C_3]^T \tag{3}$$

$$C_1 = \begin{bmatrix} \text{diag}\left(\begin{bmatrix} \theta_1 \\ \theta_2 \\ \vdots \\ \theta_n \end{bmatrix}_{n \times 1} - \alpha\right) & \text{diag}\left(\begin{bmatrix} \dot{\theta}_1 \\ \dot{\theta}_2 \\ \vdots \\ \dot{\theta}_n \end{bmatrix}\right) \\ \text{diag}\left(\begin{bmatrix} \theta_n \\ \theta_{n-1} \\ \vdots \\ \theta_1 \end{bmatrix}_{n \times 1} - \alpha\right) & \\ & \begin{bmatrix} \dot{\theta}_n \end{bmatrix}_{2n \times 1} \end{bmatrix}_{2n \times 3n}$$

$$C_2 = \begin{bmatrix} C_{21} \\ C_{22} & C_{23} \end{bmatrix}_{2n-1 \times 3n}$$

$$C_{21} = \begin{bmatrix} \theta_1 & -\theta_2 & 0 & \cdots & 0 \\ 0 & \ddots & \ddots & \ddots & \vdots \\ \vdots & \ddots & \theta_{n-1} & \theta_n & 0 \\ 0 & \cdots & 0 & 0 & 0 \end{bmatrix}_{n \times n}$$

$$C_{22} = \begin{bmatrix} \theta_n & -\theta_{n-1} & 0 & \cdots & 0 \\ 0 & \ddots & \ddots & \ddots & \vdots \\ \vdots & \ddots & \theta_3 & -\theta_2 & 0 \\ 0 & \cdots & 0 & \theta_2 & -\theta_1 \end{bmatrix}_{n-1 \times n}$$

$$C_{23} = \begin{bmatrix} \dot{\theta}_1 & -\dot{\theta}_2 & 0 & \cdots & 0 \\ 0 & \ddots & \ddots & \ddots & \vdots \\ \vdots & \ddots & \dot{\theta}_{2n-2} & -\dot{\theta}_{2n-1} & 0 \\ 0 & \cdots & 0 & \dot{\theta}_{2n-1} & -\dot{\theta}_{2n} \end{bmatrix}_{2n-1 \times 2n}$$

$$C_3 = [\beta \quad \beta \quad \cdots \quad \cdots \quad \beta \quad \beta]_{1 \times 3n}$$

$$x_{3n \times 1} = \begin{bmatrix} k_1 \\ k_2 \\ \vdots \\ k_{n-1} \\ k_n \\ b_1 \\ b_2 \\ \vdots \\ b_{2n-1} \\ b_{2n} \end{bmatrix} \tag{4}$$

$$d_{4n\times 1} = \begin{bmatrix} \tau_1 \\ \tau_2 \\ \vdots \\ \tau_{2n-1} \\ \tau_{2n} \\ \tau_1 - \tau_2 \\ \tau_2 - \tau_3 \\ \vdots \\ \tau_{2n-1} - \tau_{2n} \\ 0 \end{bmatrix} \quad (5)$$

The matrix C consists of three sub-matrices, $C_1$, $C_2$ and $C_3$. $C_1$ can be the main part responsible for the fitting of the spring and dashpot constants, k and b. $C_2$ bounds the rate of change of the passive joint torque and ensures smoothness in the resulting passive joint torque, and $C_3$ is basically a row of penalty constants, $\beta$, which penalizes large values of the spring and dashpot constants and thus limits the magnitudes of both. In this work, $\beta$ is set to 0.1.

The origin of each virtual spring can be also added to the optimization problem formulation as a parameter in order to obtain a tighter passive torque fit. Therefore, the optimization problem given by (3) can be solved iteratively for a range of values of spring origin constant, $\alpha$. The solution with the least error norm can be selected as the optimal solution.

Figure 21A:
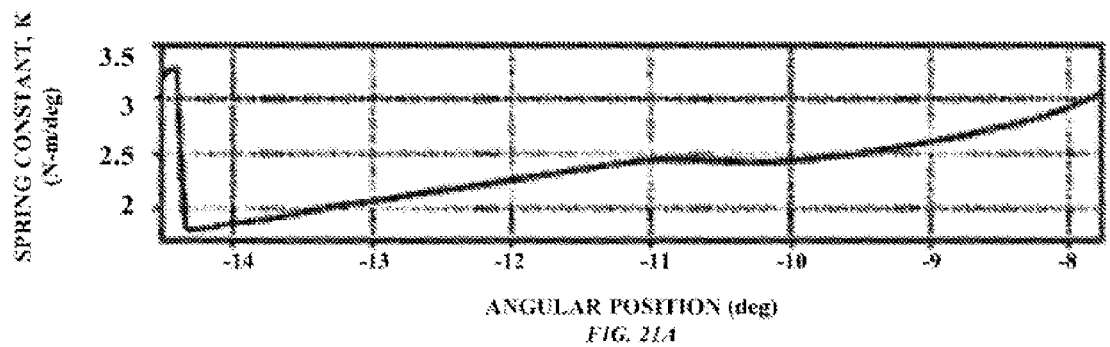
FIGS. 21A, 21B, and 21C are the output of the decomposition for Segment 1 showing, respectively, the spring constants, dashpot constants, and the active and passive knee torques.
Figure 21B:
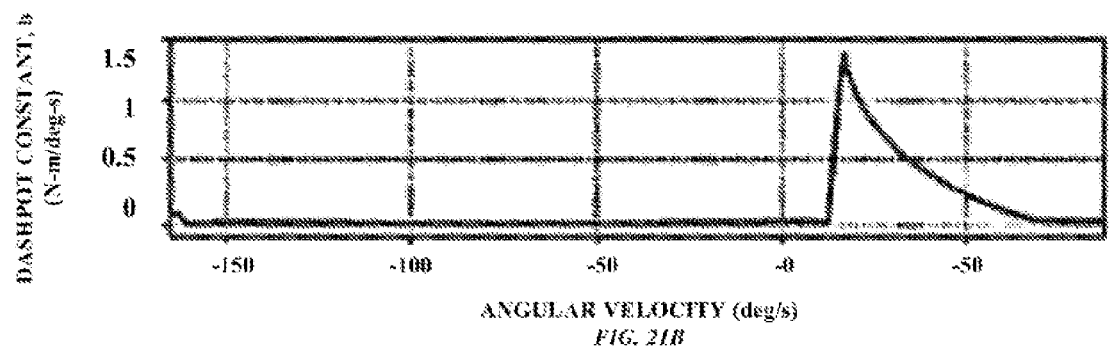
Figure 21C:
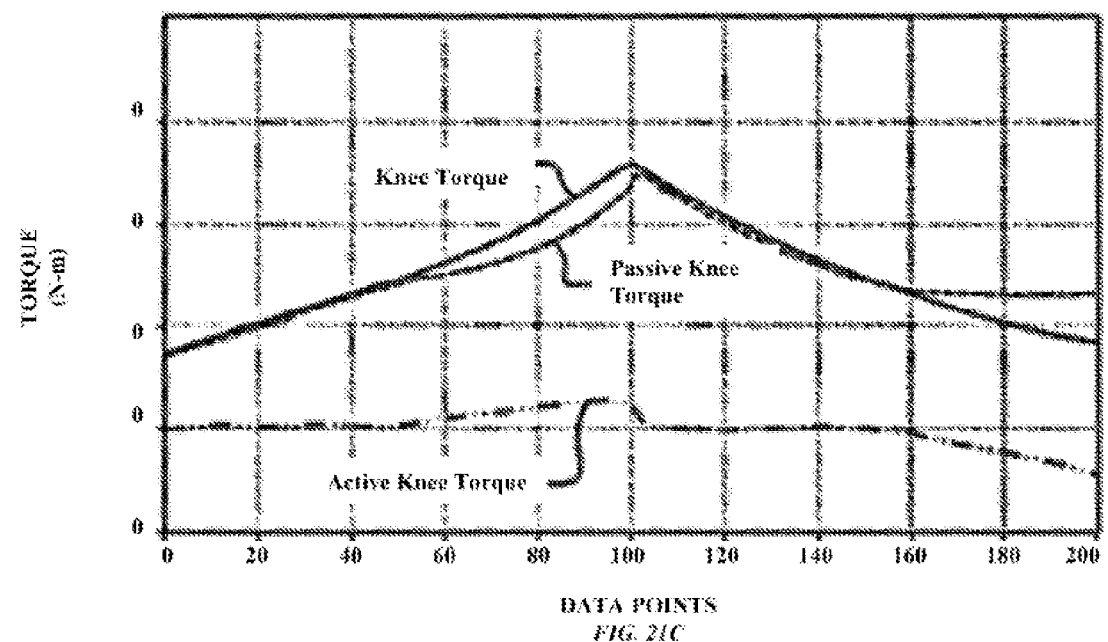
Figure 22:
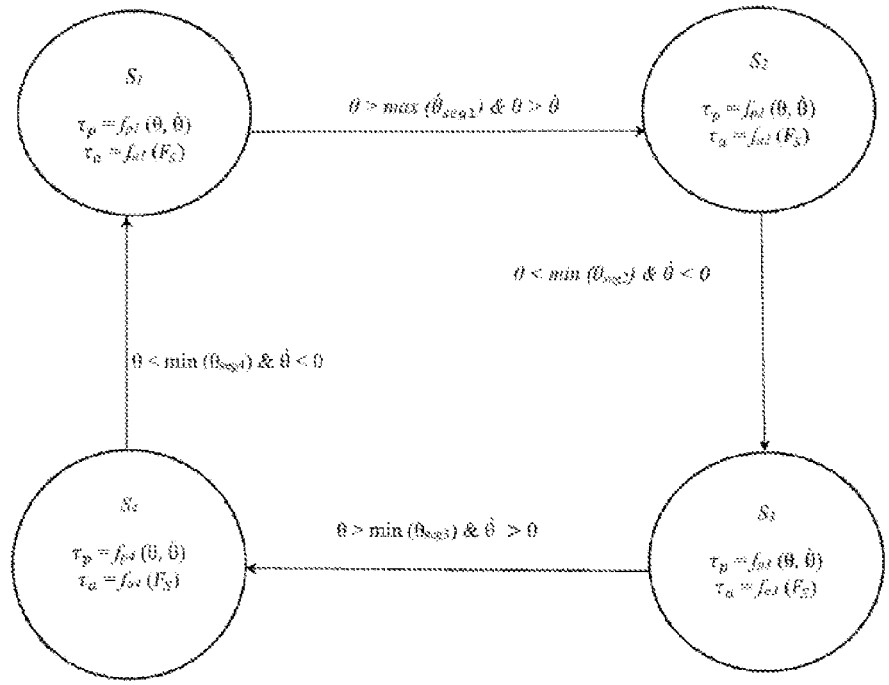
FIG. 22 is a state chart for governing the discrete dynamics of an active-passive decomposition controller in accordance with an embodiment of the invention.
Figure 23:
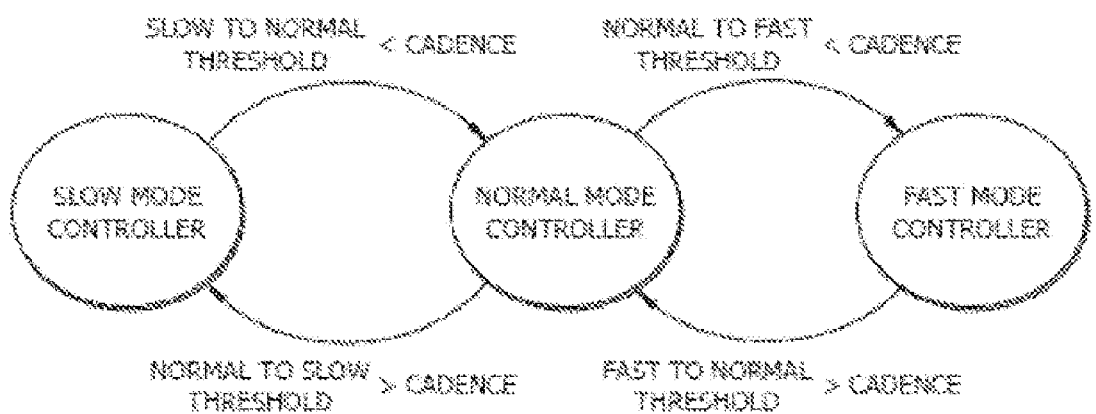
FIG. 23 is a state chart for governing the discrete dynamics of the cadence estimator in accordance with an embodiment of the invention.
Figure 24:
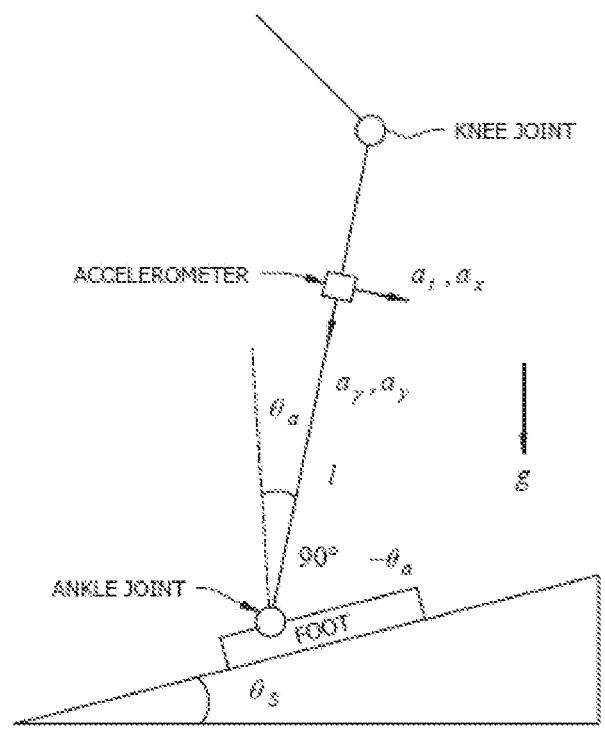
FIG. 24 is a schematic diagram of accelerometer measurements for slope estimation in accordance with an embodiment of the invention.

The result of the above stated constrained optimization problem for segment 1 can be shown in plots (a), (b), and (c) in FIG. 21. FIG. 21 is the output of the decomposition for $s_1$ in FIG. 19 showing the spring and dashpot constants and the active and passive knee torques (Spring origin, $\alpha$ is 23 degrees).

As can be seen from FIG. 21, the decomposed passive part can be very similar to the joint torque, and thus it can be stated that the behavior of the joint can be mainly passive. The result of the decomposition for the segment s, can be stored in R, of the form given in Equation 6.

$$R_i = [\theta \dot{\theta} \tau_{pas} F_{S1} F_{S2} \tau_{act}]_{2n\times 6} \quad (6)$$

where $t_{pas} = C_1 x$.

The procedure presented above decomposes the joint torques into active and passive parts. The joint torque references for the control of the prosthesis are generated by combining this active and passive torques. There are two major challenges to be solved. Firstly, the correct motion segment must be selected. Secondly, after the motion segment is selected at each sampling instant a new joint torque reference can be generated using the discrete mappings for the active and passive torque parts.

A switching system modeling approach incorporating both discrete and continuous states can be used for the reconstruction of the torque reference signal. The state chart shown in FIG. 22. will govern the discrete dynamics of the controller. Since the sequence of the segments can be ordered (i.e., the direction of the motion for a specific gait phase does not change), each segment can transition only to the next one, where the transition guard function can be written as a inequality in terms of $\theta$ and $\dot{\theta}$. The transitions between segments take no time and the dynamics of the controller are governed by the $\{f_{pi}(\theta, \dot{\theta}); f_{ai}(F_s)\}$ pair at each sampling instant. The joint reference torque is $$t_{ref} = t_a + t_p = f_{pi}(\theta, \dot{\theta}) + f_{ai}(F_S) \quad (7)$$

The decomposition algorithm presented above gives the result matrix, R, for each segment. The discrete data in R can be used to construct the joint torque reference for the continuous measurements of another trial in the same gait phase. At each sampling instant of the algorithm, the measurement vector $m = [\dot{\theta}_m, F_{S1\_m}, F_{S2\_m}]^T$ can be acquired. For the reconstruction of the passive knee torque part, the Euclidian error norm between the $[\theta_m, \dot{\theta}_m]^T$ and the angular position and velocities of all the samples in that segment $[\theta_i, \dot{\theta}_i]^T$ can be calculated as shown in Equation 8 and stored in the vector e.

$$e_i = (\theta_m - \theta_i)^2 + (\dot{\theta}_m - \dot{\theta}_i)^2 \quad (8)$$

Then two elements of this vector with the least error norm are found and the passive knee torque reference can be found as a weighted linear combination of the passive knee torques corresponding to these points. The reconstruction of the active knee torque part is similar where only $\{\theta, \dot{\theta}, t_{pas}\}$ is exchanged with $\{F_{S1}, F_{S2}, t_{act}\}$.

The supervisory controller (intent recognizer) switches among different underlying intramodal controllers depending on the activity mode the user imposes on the prosthesis. The intent recognizer consists of three parts: activity mode recognizer, cadence estimator and the slope estimator.

The activity mode recognizer detects the activity mode of the prosthesis (standing, walking, sitting, stair ascent or stair descent, etc. . . . ). This can be accomplished by comparing the features which are generated in real time to a feature database using some machine learning and/or pattern recognition methods. The present implementation of the gait mode recognizer, which recognizes standing and walking modes, is described below.

Firstly, a database which contains all the possible activity modes (standing and walking in this case) can be generated by making experimental trials. In the experimental trials, the user can be asked to walk or stand in different controller modes for 50 second long trials. The socket sagittal moment above the knee joint, foot heel load, foot ball load, knee angle, knee velocity, ankle angle and ankle velocity are recorded with 1 ms sampling period. It should be noted that other sensor signals such as accelerations and electromyography measurements from the residual limb can be added to the list of the signals used for intent recognition. For example, from the recorded experimental trials, 10000 random frames (5000 standing and 5000 walking) of 100 samples length are generated for all the seven recorded signals. The mean and the standard deviation of each frame are computed. The mean and standard deviation of signals are selected as the features since minimal computation can be required to obtain them. A database containing 10000 samples with 14 features (mean and standard deviation of the seven signals) belonging to two classes (standing and walking) can be generated. After the database is generated, the dimension of the database can be reduced from 14 to three using principal component analysis (PCA). Dimension reduction can be necessary because pattern recognition for high dimensional datasets can be computationally intensive for real-time applications. After dimension reduction state, the standing and walking data can be modeled with Gaussian mixture models. Gaussian mixture models represent a probability distribution as a sum of several normal Gaussian distributions. The order of the Gaussian mixture model for each mode can be determined according to the Minimum Description Length Criteria.

As described above, the database generation, dimension reduction and the Gaussian mixture modeling are explained. For real-time decision making, overlapping frames of 100 samples can be generated at each 10 ms interval. 14 features described above are extracted from these frames and the PCA dimension reduction can be applied to these features to get a reduced three dimensional feature vector. The reduced dimension features can be fed to the Gaussian mixture models for standing and walking and the probability of the sample vector being standing or walking can be computed. The mode with the greater probability is selected as the instantaneous activity mode. Since one decision might give wrong results in some cases due to noise, disturbance, etc. . . . , a voting scheme can be used to enhance the results. In the voting scheme, the controller activity mode is switched if and only if more than 90 percent of the instantaneous activity mode decisions among the last 40 decisions are a specific activity mode.

Once a new activity mode is selected by the voting scheme, the underlying activity controller can be switched to the corresponding mode.

Such an activity mode recognizer is provided by way of illustration and not as a limitation. In the various embodiments of the invention, one or more parts of the algorithm might be modified. For example, in some embodiments, different features such as mean, max, kurtosis, median, AR coefficients, wavelet based features, frequency spectrum based features of the frame might be generated. Additionally, different dimension reduction techniques such as linear discriminant analysis, independent component analysis might be employed. Furthermore, different classification methods such as artificial neural networks, support vector machines, decision trees, hidden Markov models might be used.

Cadence estimation is accomplished by observing peak amplitudes in characteristic signal data and then measuring the time between successive peaks. Since walking is a cyclic activity each of the sensor signals will be periodic of cadence. The most relevant sensor signals will contain only one characteristic amplitude peak per stride such as foot heel load and the ball of foot load. In the real-time implementations, cadence estimation is accomplished by recording the foot load after heel strike when it exceeds 400 N until the load decreases below 350 N. Then, the time of occurrence of the peak load in this window is found and the previous peak time is subtracted from the new peak time. This corresponds to stride time and can be converted to cadence (steps/min) by multiplying with 120. Once the cadence is estimated, the intent recognizer selects the corresponding middle layer controller based on some predefined thresholds as in FIG. 23.

For example, in some embodiments, a 3D accelerometer capable of measuring ±3 g accelerations is embedded into the ankle joint coupler where the prosthetic foot is connected. An exemplary arrangement of such a system is shown by the schematic in FIG. 24. The accelerometer measurements are used to estimate the ground slope. In order to estimate the ground slope, the accelerometer data in tangential direction is used. Assuming the foot is flat on the ground, the ground slope angle, $\theta_s$, can be calculated as in equation (9) below.

$$\theta_s = \sin^{-1}\left(\frac{\alpha_t}{g}\right) \quad (9)$$

Figure 25:
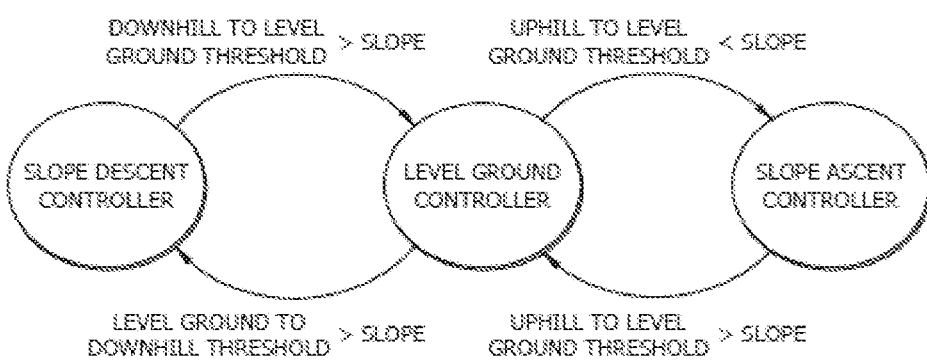
FIG. 25 is a state chart for slope estimation in a controller in accordance with an embodiment of the invention.
Figure 26:
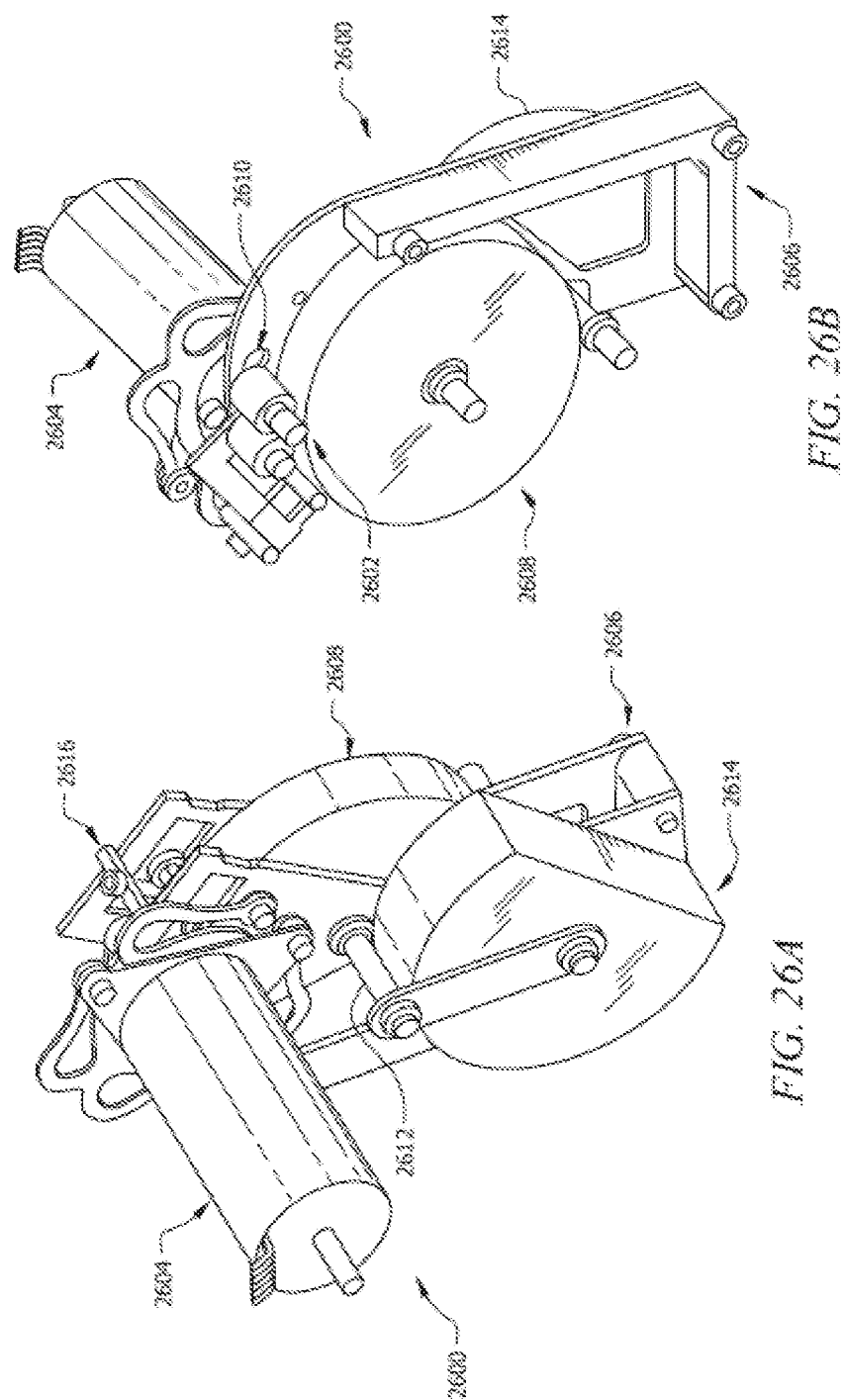
FIGS. 26A and 26B show front and back views of a friction/cable drive motor in accordance with an embodiment of the invention.

In Eqn. 9, g is the gravitational constant. In order to find the ground slope estimate, $\hat{\theta}_S$, the accelerometer data should be collected while the foot is flat on the ground as determined by the heel and ball of the foot load sensors. While the foot is flat on the ground, equation (1) is computed for the frame of the collected data and the mean of this frame is outputted as the ground slope estimate, $\hat{\theta}_S$. Once the slope is estimated, the intent recognizer selects the corresponding middle layer controller based on some predefined thresholds. An exemplary state chart for such an intent recognizer is shown in FIG. 25.

Rather than a ballscrew and slider crank embodiment for the transmission of torque from a motor to the ankle and/or knee units, in some embodiments of the invention, the prosthesis can incorporate a friction and cable drive transmission embodiment. FIGS. 26A and 26B show front and back views of an exemplary embodiment of a friction drive transmission 2600 in accordance with an embodiment of the invention. As shown in FIGS. 26A and 26B, the shaft 2602 of an electric motor 2604 is preloaded against a first stage in a housing 2606, such as a larger diameter cylinder or friction drive gear 2608, which creates sufficient friction to transmit torque without slip. The shaft 2602 can use one or more friction rollers 2610 to transmit the torque. The first stage of the friction drive can also be supplemented with a second stage. The friction drive gear 2608 drives a smooth pinion 2612 directly, which is preloaded against a larger diameter cylinder or cable gear output 2614 in the housing 2606, which in turn transmits torque directly to the knee or ankle joint.

In addition to, or rather than a friction drive, the first or second stage of the transmission can alternatively be embodied by a cable drive transmission, in which a cable is wrapped around the circumference of a larger diameter cylinder, such as friction drive gear 2608, and also around the circumference of a smaller diameter cylinder, such as pinion 2612. In such embodiments, the cable is affixed to the friction drive gear 2608, and is pretensioned, using a tensioning screw 2616 or similar means, around both the drive gear 2608 and pinion 2612, such that friction between cable and pinion 2612 enables the transmission of torque from between the pinion 2612 and drive gear 2608. In one embodiment of a combined friction drive/cable drive transmission can be used, in which a first stage of the transmission (i.e., the friction drive gear 2608 connected directly to the electric motor 2604) is of the friction drive type, while the second stage of the transmission (i.e., the cable gear output 2614 connected directly to the knee or ankle joint) is of the cable drive type.

Rather than the ballscrew and slider crank or the friction drive and cable drive embodiments for the transmission of torque from a motor to the ankle and/or knee units, in some embodiments of the invention, the prosthesis can incorporate a chain drive or a belt drive transmission embodiment for implementing one or more stages of a transmission.

Advantages of a belt or chain drive approach over the ballscrew approaches described above include the ability to provide a fully enclosable/sealable (without need for a bellows-type cover) powered leg device. This facilitates component immersion in lubricating environment, and well as facilitating isolation from dirt, water, and other debris. As a result, this can extend the lifetime of transmission components. Another advantage of such a configuration is that it enables a greater range of motion of joint actuation, as opposed to a slider-crank mechanism (as used in a ballscrew configuration), which is generally limited. Further, the belt or chain drive approach also allows the device to maintain a constant transmission ratio throughout range of motion, which is not generally possible in the slider-crank mechanism typically used in a ballscrew configuration. Additionally, advantages of a belt or chain drive approach is that it maintains constant mechanism geometry throughout range of motion, belt and chain drive components are typically less expensive than ballscrew components, and belt and chain drive systems are typically characterized by lower audible noise than ballscrew configurations.

Figure 27:
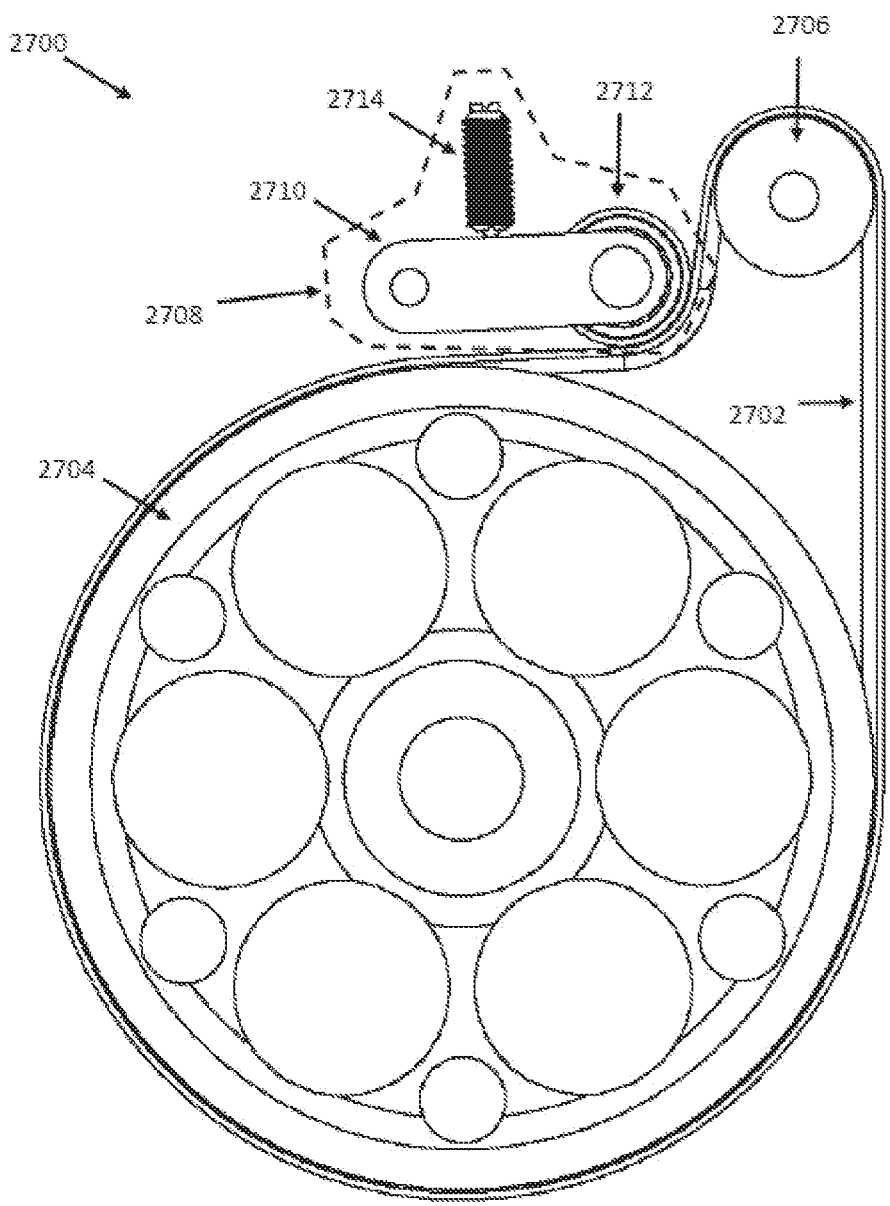
FIG. 27 shows an exemplary embodiment of a belt drive transmission in accordance with an embodiment of the invention.

FIG. 27 shows an exemplary embodiment of a belt drive transmission 2700 in accordance with an embodiment of the invention. As shown in FIG. 27, a stage of the transmission 2700 can be embodied as a belt drive transmission, in which a belt 2702 is wrapped around the circumference of a larger diameter shaft, such as a first belt gear or pulley 2704, and also around the circumference of a smaller diameter shaft, such as second belt gear or pulley 2706. In such embodiments, the belt 2702 can be tensioned, using a tensioning device 2708. In one embodiment, the tensioning device 2708 can consist of a swing arm 2710, an additional pulley 2712 attached to the end of swing arm 2710, and tensioning screw 2714 for adjusting the swing arm 2710 to bias the additional pulley 2712 against the belt 2702, such that friction between the belt 2702 and belt gears 2704 and 2706 enables the transmission of torque from between second belt gear 2706 and first belt gear 2704. However, any other type of tensioning device can be used in the various embodiments to tension the belt 2702. For example, in some embodiments, the tensioning device 2708 can be a spring loaded device to automatically bias a pulley 2706 or other object against belt 2702 to cause the necessary tension.

It is worth noting that although transmission 2700 is illustrated in terms of a V-belt embodiment, the invention is not limited in this regard and can be used with any type of belts. For example, the belt 2702 can also be embodied as a flat belt, a round belt, a multi-groove belt, a ribbed belt, and a toothed or cog belt, to name a few. Further, the belt gears 2704 and 2706 can be configured in accordance with the type of belt being used.

In some embodiments, rather than utilizing a belt-based drive, a chain-based drive can be provided. The configuration in such embodiments can be substantially similar to that shown in FIG. 27. That is, a chain can be provided in place of belt 2702 and gears 2704 and 2706 can be embodied as sprockets compatible with the chain. In such embodiments, the tensioning device 2708 described above can still be utilized to maintain proper tension of the chain to enable the transmission of torque from between sprockets in the transmission.

In some embodiments, instead of utilizing a tensioning device as described above with FIG. 27, a pulley or sprocket can be configured with an eccentric mount. That is, configuring at least one of the drive gears in the transmission to allow an adjustment of its position. This is illustrated below with respect to FIGS. 28A-28D.

Figure 28A:
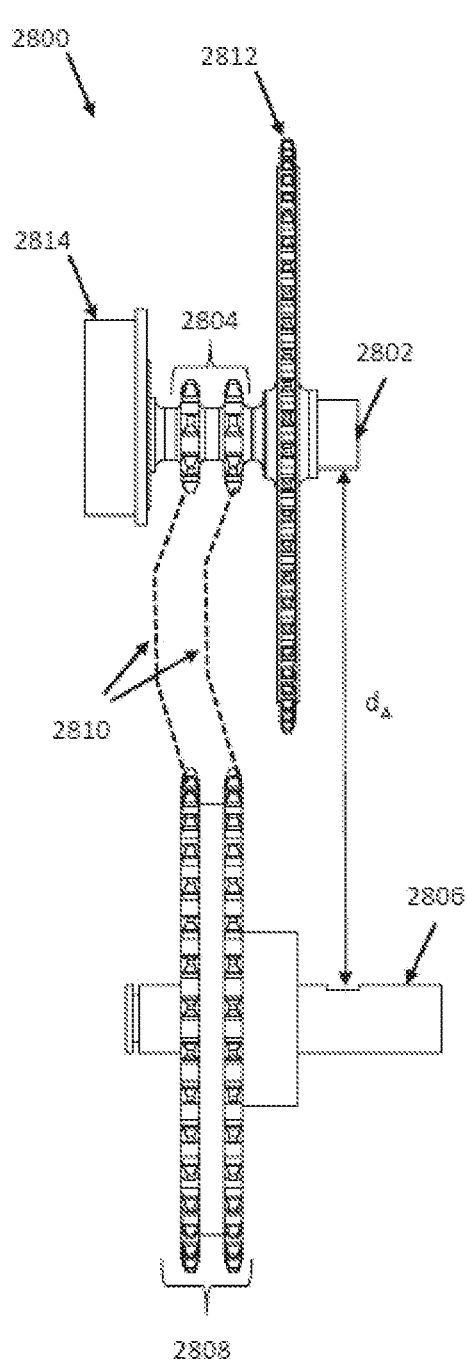
FIGS. 28A and 28B show side views of first and second positions, respectively, achievable for an exemplary embodiment of a chain drive transmission including an eccentric mount in accordance with an embodiment of the invention.
Figure 28B:
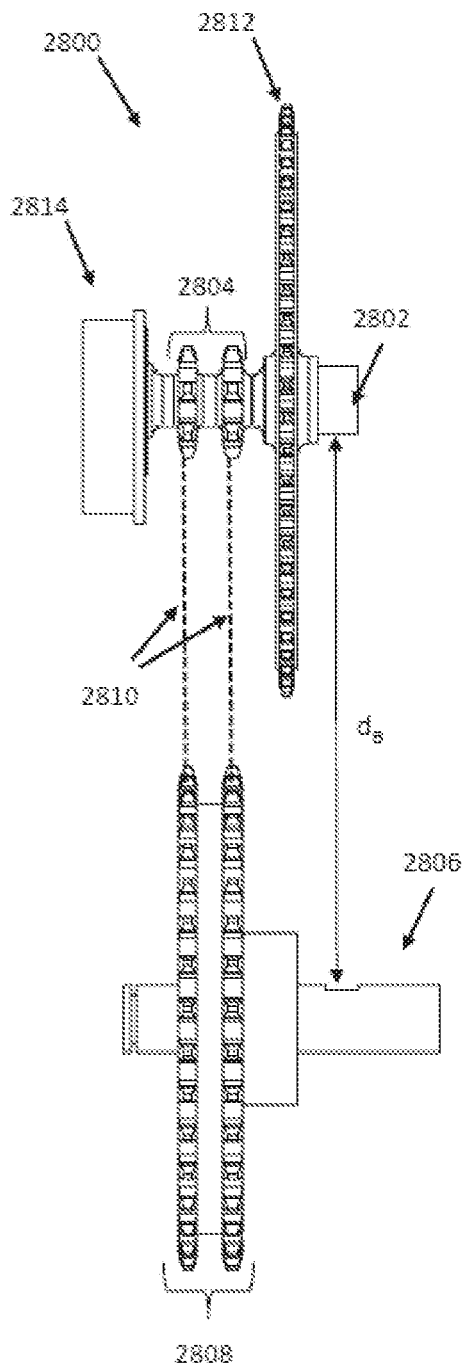

FIGS. 28A and 28B show side views of first and second positions, respectively, achievable for an exemplary embodiment of a chain drive transmission 2800 including an eccentric mount in accordance with an embodiment of the invention. Similar to the transmission described above with respect to FIG. 27, transmission 2800 includes a first shaft 2802 with first drive gears or sprockets 2804 and a second shaft 2806 with second drive gears or sprockets 2808 which can be coupled together via chains 2810 to transmit torques between sprockets 2804 and sprockets 2808. Although FIGS. 28A and 28B show that the transmission of torque between sprockets 2804 and sprockets 2808 is performed using two sets of sprockets (and thus using two chains), the embodiments are not limited in this regard. Rather, any number of chains can be used in the various embodiments.

As shown in FIGS. 28A and 28B, the first shaft 2802 is shown as including an additional sprocket 2812 for driving first shaft 2802. Such a configuration can be used when multiple drive stages are provided. However, the various embodiments are not limited in this regard.

In transmission 2800, the first shaft 2802 is configured to be eccentric. That is, the position of the first shaft 2802 is adjustable relative to the position of the second shaft 2806 so as to adjust the lateral separation between the shafts (i.e., to provide $d_A \neq d_B$). Accordingly, this also provides a means to adjust the tension in a chain (or a belt) between the first shaft 2802 and the second shaft 2806. To provide the eccentric mount, the first shaft 2802 can be mounted in a leg device to an adjustable bearing mount 2814. The operation and configuration of an exemplary embodiment of the adjustable bearing mount 2814 is illustrated with respect to FIG. 29.

Figure 29:
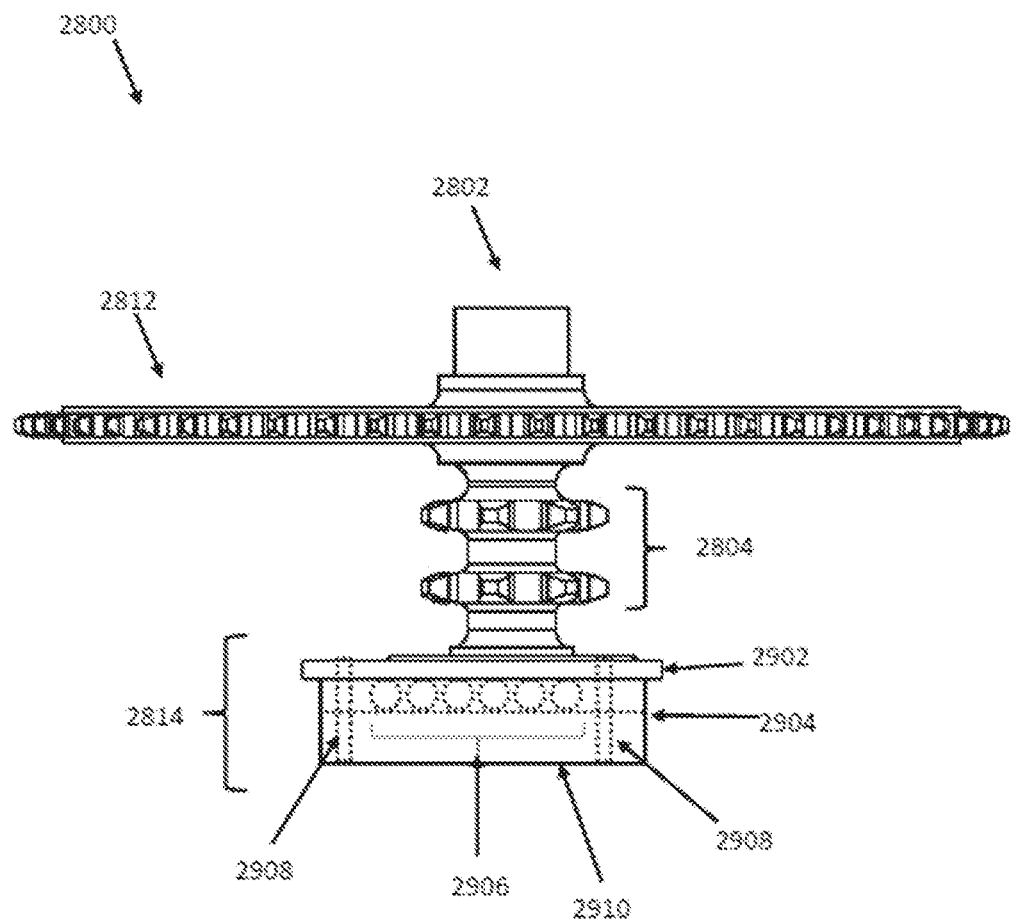
FIG. 29 illustrates schematically the components for the adjustable bearing mounts in FIGS. 28A and 28B.

FIG. 29 illustrates schematically the components for the adjustable bearing mount 2812. As shown in FIG. 29, the adjustable bearing mount 2814 can include a top plate 2902 to which first shaft 2802 is attached, a bottom plate 2904, bearings 2906 between the top plate 2902 and the bottom plate 2904, and fasteners 2908. These components of the adjustable bearing mount 2814 can be disposed within an enclosure 2910.

In FIG. 29, the fasteners 2908 are shown as screws or bolts. However, the various embodiments are not limited to any particular bearing type or design of screws or bolts and other bearing types or designs can be used without limitation. Further, the various embodiments are not limited to screws or bolts and any other type of removable fastener can be used without limitation. Additionally, FIG. 29 shows bearings 2906 as a collection of ball bearings disposed between plates 2902 and 2904. However, the various embodiments are not limited to any particular bearing type or design and other bearing types or designs can be used without limitation.

In operation, the enclosure 2910 can be configured such that when fasteners 2908 are loosened or removed, the bearings allow the top plate 2902 can be repositioned relative to the bottom plate 2904 via bearings 2906. Thus, when fasteners 2908 are replaced and tightened, the plates 2902 and 2904 are biased against bearings 2906 to prevent further motion of the top plate 2902 relative to the bottom plate 2904.

Such a configuration allows adjustment of the position of first shaft 2802. For example, this can allow the first shaft 2802 to transition between a first position, as shown in FIG. 28A, in which a chain or belt 2810 with reduced tension is provided, due to a reduced distance ($d_A$) between first shaft 2802 and second shaft 2806, to a second position, as shown in FIG. 28B, in which a chain or belt 2814 with increased tension is provided, due to an increased distance ($d_B$) between first shaft 2802 and second shaft 2806. However, the various embodiments are not limited to solely first and second positions. Rather, in the various embodiments, the adjustable bear mount 2812 can be configured to allow a variety of positions for the first shaft 2806 relative to the second shaft 2806.

Figure 30:
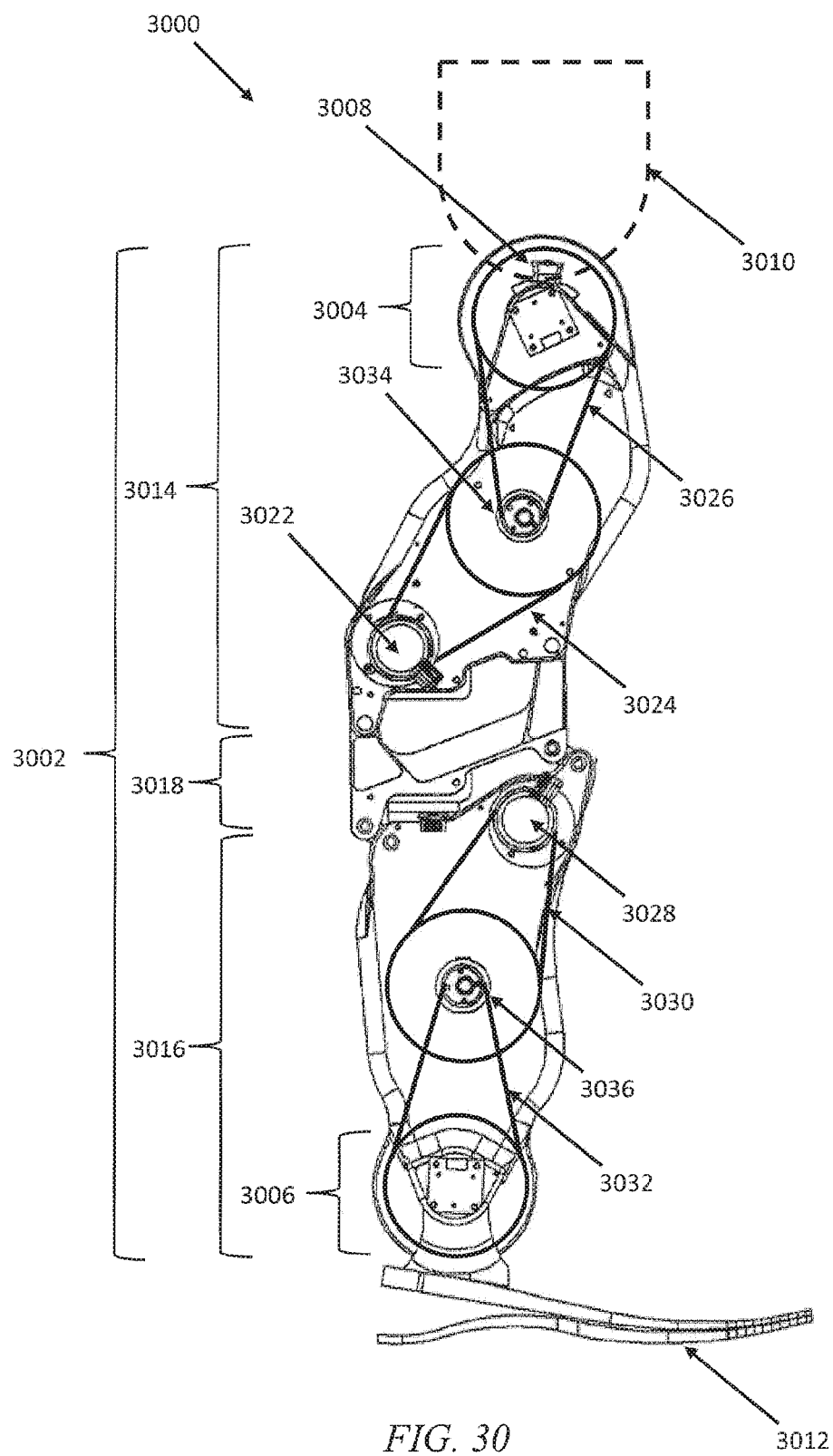
FIG. 30 illustrates an exemplary configuration of a powered leg prosthesis in accordance with the embodiments shown in FIGS. 27-29.

An exemplary configuration of a powered leg prosthesis 3000 in accordance with the discussion above is illustrated schematically in FIG. 30. As shown in FIG. 30, the powered leg prosthesis 3000 includes a shank 3002 with a powered knee joint 3004 and a powered ankle joint 3006. The powered knee joint 3004 includes a socket interface 3008 for attaching a socket 3010 or other device for attachment of the powered leg prosthesis 3000 to an amputee. The powered ankle joint 3006 can have a foot portion 3012 attached thereto.

The shank 3002 can consist of a single, discrete unit. However, in some embodiments, the shank can include an upper portion 3014 and a lower portion 3016. Such a configuration allows the insertion of at least one extension unit 3018 to allow the length of the shank 3002 to be customized for the amputee.

Within each of the upper portion 3014 and the lower portion 3016, a belt or chain drive system can be implemented, as described above with respect to FIGS. 27-29. For example, as shown in FIG. 30, the upper portion 3014 can include a first motor 3022, a first upper drive stage 3024, and a second upper drive stage 3026 for providing power at the powered knee joint 3004. Similarly, the lower portion 3016 can include a second motor 3028, a first upper drive stage 3030, and a second upper drive stage 3032 for providing power at the powered ankle joint 3006. Each stage can consist of the belt or chain drive stage. Additionally, each stage can be configured to include an eccentric mount, such as mounts 3034 and 3036, to adjust tension in the upper portion 3014 and lower portion 3016 respectively.

In addition to the components described above, the powered prosthetic leg 3000 can include other components not illustrated in FIG. 30 for purposes of clarity. For example, the powered prosthetic leg can include a control system or device, as previously described, and one or more sensors throughout the powered prosthetic leg, also as previously described. Thus control of the powered prosthetic leg 3000 can occur in substantially the same manner as described above.

Stair Controller

Now that the configuration and operation of a single powered prosthesis has been described, the disclosure now turns to a description of the stair controller in accordance with the various embodiments. It should be noted that the examples and results presented below are provided solely for illustrating the various embodiments and are not intended to limit the various embodiments in any way.

The gait patterns seen in healthy humans navigating stairs and steps is fundamentally distinct from level ground walking. Most notably, in biomechanically proper stair ascent the stance phase in the lower limb begins with significant knee flexion and ends near hyperextension. It is primarily this net knee extension during the stance phase that lifts the subject up the step. In healthy subjects this knee extension is not passive, rather the knee actively supplies a torque to lift the subject. Contrarily, in level ground walking the knee typically leaves stance slightly more flexed than when it entered, as the knee has already begun the flexing process that will continue through early swing. Additionally, the energetic behavior of the knee in the stance phase of level ground walking is primarily dissipative in nature, the opposite of the energetic behavior of the knee in stair ascent.

In the same way that the lower limb produces a net knee extension in stance for stair ascent, a net knee flexion is typically seen in stair descent. This flexion allows the subject to lower his or her center of mass in anticipation of landing the contralateral foot on the subsequent step. Although the knee ends stance with more flexion than it enters stance during level ground walking, the amount of net knee flexion is greater in stair descent. A more distinct difference between level ground walking and stair descent, however, can be seen in the ankle behavior during both swing and stance. At the end of swing the ankle actively plantarflexes in anticipation of a forefoot strike on the subsequent step. This preparatory plantarflexion decreases the single support phase by allowing the foot to strike the step sooner. Additionally, it provides an extended range of motion for damping and impact absorption to occur in the following stance phase. This behavior is distinct from level ground walking as the foot experiences a heel strike at the end of swing and dissipates energy with an opposite motion to that seen in stair descent.

Due to the significant biomechanical differences between both stair ascent and stair descent relative to level ground walking, distinct control systems can be implemented for powered prostheses in order to properly reproduce the biomechanical behaviors seen in healthy subjects. Both stair ascent and stair descent require periods of significant positive power delivery from both joints, and therefore are best served by prostheses that can provide such power through a carefully designed control system.

In stair ascent, the stance phase can be divided into a period of active knee extension, where the knee is delivering power to the user to lift him or her up the step, and then subsequently by a period of active ankle extension, where the ankle plantarflexes when the knee is straight and the user gains further height over the next step and the stance leg prepares for the knee flexion of the swing phase. These two periods of power delivery appear distinct in healthy biomechanics and therefore their separation in the control of a powered prosthesis can better emulate the healthy subject strategy. The swing phase of the stair ascent can be divided into distinct periods of swing flexion and swing extension. These motions could be generated by emulating a passive impedance at each joint, but it is not integral to the invention to do so. An alternative strategy to achieve swing is to execute a predefined trajectory at the knee and/or ankle joint.

In stair descent, the stance phase can be divided into a period of ankle yielding, where the ankle dissipates energy, and then subsequently by a period of knee yielding, where the knee dissipates energy. These two periods of power dissipation appear distinct in healthy biomechanics and therefore their separation in the control of a powered prosthesis can better emulate the healthy subject strategy. The swing phase for stair descent can be divided into distinct periods of swing flexion and swing extension. These motions could be generated by emulating a passive impedance at each joint, but it is not integral to the invention to do so. An alternative strategy to achieve swing is to execute a predefined trajectory at the knee and/or ankle joint.

In some embodiments, it may be necessary to transition into or out of the stair ascent controller or the stair descent controller from or into a distinct controller for a separate lower limb activity. In this case a suitable cue must be identified in order to instigate such a transition. Cues can be based off of any sensor information available to the prosthesis, including, but not limited to: (1) estimating the location of a segment of the prosthesis or the user with respect to gravity through the use of inertial measurement; (2) joint angle or angular velocity measurements; (3) measurements of the degree of load or moment bearing in the prosthesis; and (4) direct input from the user, such as pressing a button or using a remote control.

In certain embodiments, feedback regarding the activity mode can be provided. For example, feedback can be provided to the user in the form of a tactile vibration from the prosthesis. This feedback can serve a variety of purposes with respect to informing the user of the decisions made by the control system. In one embodiment of the control system, tactile feedback can be given upon entering either the stair ascent or stair descent portion of the controller in order to inform the user of this transition.

I. Stair Controller Model

In the various embodiments, the stair controller can be implemented using activity-level controllers in the form of a finite state machine (FSM). Each state within the FSM generates torque commands for the knee and ankle joints that ensure passivity within the state. The torque command is a function of joint angular position and velocity, and is given by $$\tau_k = k_k(\theta_k - \theta_{eq_k}) + b_k \dot{\theta}_k \quad (10)$$

and $$\tau_a = k_a(\theta_a - \theta_{eq_a}) + b_a \dot{\theta}_a, \quad (11)$$

Where t denotes the commanded torque, 0 denotes the joint angle, and θ denotes the joint angular velocity. The subscripts k and a denote knee and ankle, respectively. The remaining parameters in each equation are easily recognized in this form as a stiffness term, equilibrium position, and a damping coefficient (k, $\theta_N$, and b, respectively). This control law, therefore, can be viewed as an emulation of a spring and damper within each state. The primary goal behind implementing such a controller is that the behavior of the prosthesis within any given state will be passive, yet energy can be introduced into the system by changing the potential energy of the virtual spring arbitrarily during transitions between finite states. Since state transitions are based on mechanical cues from the user, the user retains control over the introduction of power into an otherwise passive system.

A. Stair Ascent Controller

Figure 31:
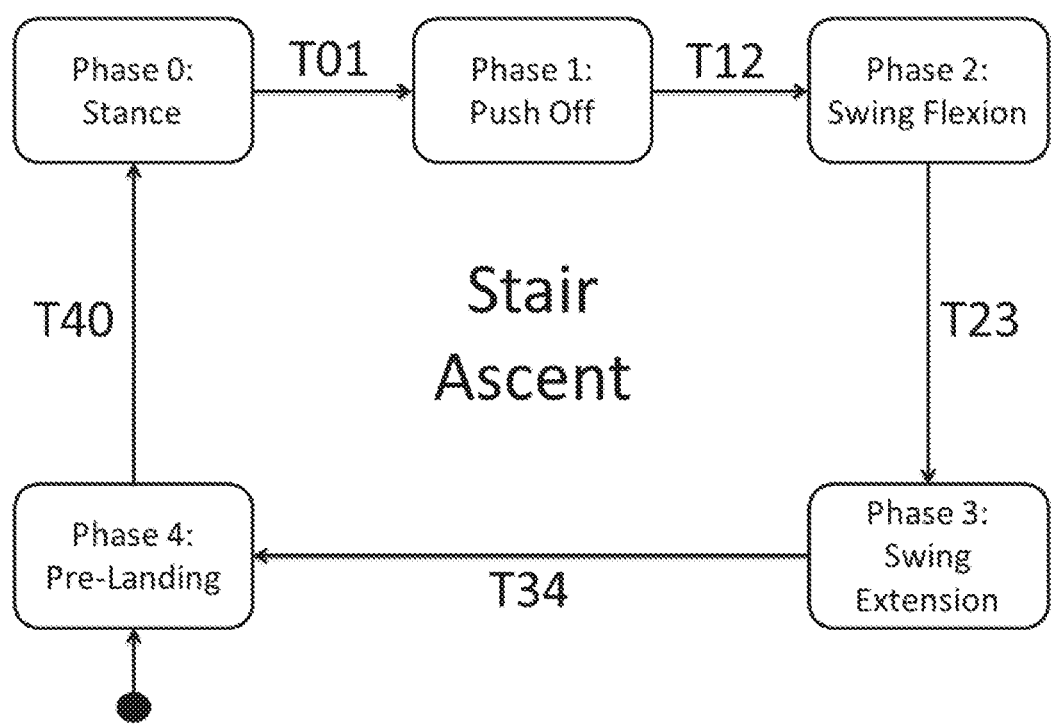
FIG. 31 illustrates a finite state machine for stair ascent in accordance with the various embodiments.

The stair ascent controller consists of 5 phases, each of which is accessed sequentially in a single stride of stair ascent. The conditions for state transitions for stair ascent are listed in Table I, and the state machine is depicted in FIG. 31.

TABLE I

Finite State Transitions for the Stair Ascent Controller

| Transition | Description | Conditions |
| --- | --- | --- |
| T01 | The knee is straightened and ankle push-off begins. | Load is high<br>Knee is straight<br>Ankle is close to zero |
| T12 | Toe leaves the ground after pushing off. | Load is low |
| T23 | Knee reaches maximum flexion in swing. | Knee velocity inflects<br>Knee exceeds a certain angle |
| T34 | Knee finishes extending and prepares for foot landing. | Knee returns to proper angle |
| T40 | Ground contact is established and the next stride begins. | Load is high |

Stair ascent begins in Phase 4, which is called the prelanding phase. In this phase, the knee angle will generally be greater than zero. This phase is tuned for a relatively high impedance to prepare the prosthesis for loading once the user positions the prosthetic foot on the first step. This high impedance allows the user to register a load on the prosthesis even though the knee is relatively bent. The registration of this load triggers the T40 transition (Load>Threshold), and the prosthesis enters Phase 0.

Phase 0 is the main power delivery phase of the stair ascent controller. In this phase, the knee extends and lifts the center of mass of the user. The knee extension is achieved by selecting a high impedance for the knee and choosing an equilibrium position near zero (i.e., to begin straightening out the leg) such that the knee generates a large moment at the beginning of this phase. The transition from Phase 0 to Phase 1 (T01) occurs when the knee and ankle angles both straighten significantly (i.e., Knee angle≈0°, Ankle Angle≈0°, with respect to FIG. 7). This straightening is due in part to the extensive knee torque provided by the impedance set in Phase 0, and also by a simultaneous exertion of hip torque in flexion from the user. This torque coincides with ground contact on the contralateral side and is the signal for the ankle to start pushing off in preparation for swing.

Phase 1 is characterized by ankle push-off, while a relatively high stiffness with an equilibrium position near zero is maintained at the knee. The transition from Phase 1 to Phase 2 (T12) occurs when ground contact is lost, as measured by a minimum threshold in the load sensor (Load<Threshold). In the various embodiments, the transitions T12 and T40 can be based on the same or different thresholds. Different thresholds can be provided since one transition is associated with loading (detected at the start of loading, which is a low level of load) and one transition is unloading (detected at a high level of load).

Phase 2 is characterized by a large knee flexion produced by a moderate impedance and a non-zero knee equilibrium angle. The non-zero knee equilibrium angle in Phase 2 is provided to allow the prosthesis to clear the stair when swung. The transition from Phase 2 to Phase 3 (T23) then occurs when the knee velocity inflects during swing. In particular, after the knee angle passes its equilibrium position (Knee Angle>$\theta_{eg}$+Δ).

Phase 3, the swing extension phase, is characterized by a knee extension, while the ankle is maintained at or near a neutral or slightly dorsiflexed angle. The knee extension is achieved by selecting a low impedance for the knee and reducing the equilibrium position such that the knee generates a moment at the beginning of this phase. The ankle position is maintained by maintaining the previous set point and stiffness. The transition from Phase 3 to Phase 4 (T34) is then triggered once the knee has extended sufficiently (Knee Angle≈$\theta_{eg}$).

In Phase 4, the knee and ankle angles are maintained with moderate impedances.

B. Stair Descent Controller

The stair descent controller is similar in form to the ascent controller, although with several significant differences in the nature of the finite states. The first major difference is that the lifting portion of the stance phase is replaced with a lowering portion as the user's center of mass moves down the steps. The second difference is that there is no push-off phase for the ankle; the small amount of swing flexion seen at the knee is actively provided by the knee actuator.

Figure 32:
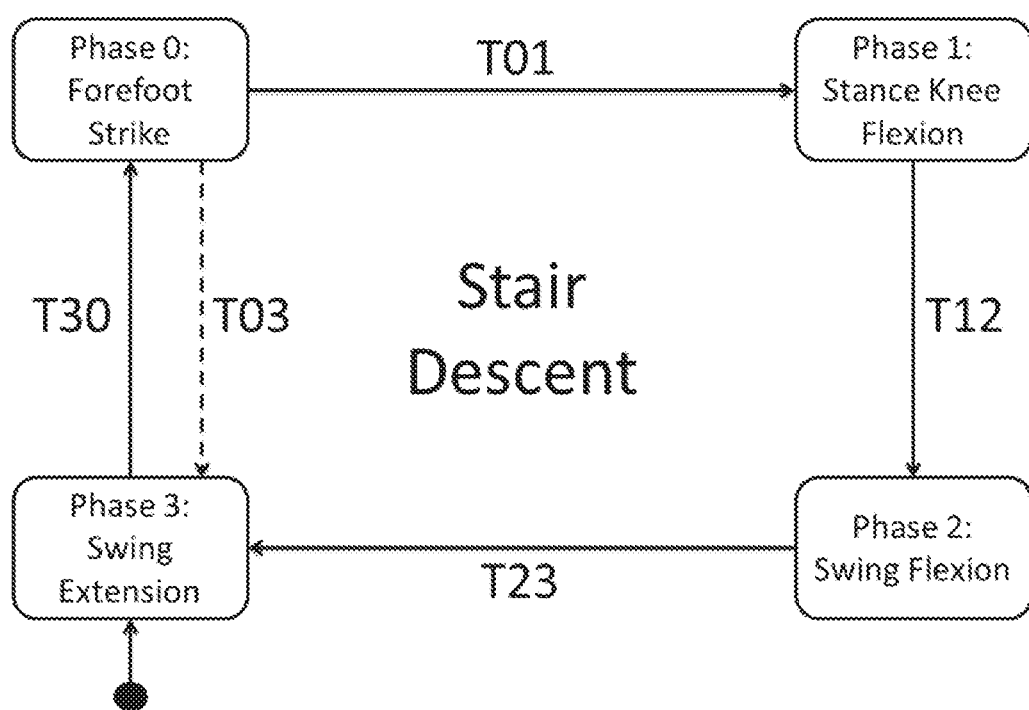
FIG. 32 illustrates a finite state machine for stair descent in accordance with the various embodiments.

The conditions for state transitions for stair descent are listed in Table II, and the state machine is depicted in FIG. 32.

TABLE II

Finite State Transitions for the Stair Descent Controller

| Transition | Description | Conditions |
| --- | --- | --- |
| T01 | The ankle finishes conforming to the ground and knee flexion begins. | Ankle is sufficiently flexed |
| T12 | Stance is reached on the contralateral limb, begin swing flexion. | Load is low<br>Knee is sufficiently flexed |

TABLE II-continued

Finite State Transitions for the Stair Descent Controller

| Transition | Description | Conditions |
|---|---|---|
| T23 | Maximum flexion is reached, begin knee extension. | Knee velocity inflects |
| T30 | Forefoot strike is detected and the next stride begins. | Load is high |
| T03 | If the foot landing phase is aborted, return to the end of swing. | Load is low |

The prosthesis enters stair descent in Phase 3, the swing extension phase. This phase is characterized by an extension of the knee to a zero equilibrium angle and a moderate impedance. Additionally, the ankle equilibrium position is selected such that the foot is substantially plantarflexed in anticipation of ground contact. This phase serves both as the phase that extends the knee at the end of a stride and also as the pre-landing phase for the next instance of ground contact. The reason that the pre-landing phase and the knee extension phase are not distinct in the stair descent controller is because a high impedance is not necessary on ground contact, since the leg is preparing to yield to the weight of the user. The transition from Phase 3 to Phase 0 (T30) then occurs when a ground contact is established, as measured by the load cell or other load sensors on the prosthesis.

At Phase 0, the prosthesis enters the forefoot strike phase. This phase is characterized by a moderate impedance in the knee and a highly damped ankle. Following forefoot strike, the ankle dorsiflexes in a highly damped manner under the load of the user, and acts to soften the impact of the user's heel with the stair. Since the ankle begins this phase in plantarflexion, it will now passively flex as the user loads the prosthesis. The transition from Phase 0 to Phase 1 (T01) will then occur when a threshold is met with respect to the ankle angle.

At Phase 1, the stance phase, the knee is highly damped, while the ankle remains damped. The result is a net knee flexion produced by the weight of the user, allowing him or her to descend the step. There is no push off phase after stance. Thus, the transition from Phase 1 to Phase 2 (T12) occurs when ground contact is lost, as measured by a minimum threshold in the load sensor (Load<Threshold).

Phase 2 is characterized by a large knee flexion produced by a moderate impedance and a non-zero knee equilibrium angle. Swing knee flexion is therefore active in this controller, although the amount of additional flexion after stance is minimal (just enough to enable the prosthesis to clear the step). The large knee equilibrium angle in Phase 2 is provided to allow the prosthesis to clear the stair when swung. The transition from Phase 2 to Phase 3 (T23) then occurs when the knee velocity inflects during swing. In particular, after the knee angle passes its equilibrium position (Knee Angle>$\theta_{eq}+\Delta$).

Phase 3, the swing extension phase, is characterized by a knee extension and an active ankle plantarflexion. The knee extension is achieved by selecting a low impedance for the knee and reducing the equilibrium position such that the knee generates a moment at the beginning of this phase. The active ankle plantarflexion is achieved by setting a plantarflexed equilibrium position with a moderate amount of stiffness and damping.

II. Stair Controller Model Validation/Verification

The controllers described above were implemented using a lower limb prosthesis similar to that described above with respect to FIG. 30. In particular, this lower limb prosthesis was configured to include knee and ankle actuators that are brushless DC motors, controlled by custom servo-amplifiers integrated into the embedded control system. Sensors in the prosthesis included a shank axial load sensor, angle sensors at the knee and ankle joints, and a 6-axis inertial measurement unit. The embedded electronics were contained on a single printed circuit board located on the shank of the prosthesis (excluding small circuit boards required for sensor interfacing). The power source was a lithium-polymer battery, and the prosthesis attaches to an amputee's socket with a standard pyramid connector. The current prototype can achieve approximately 100 Nm of torque at the ankle joint and 90 Nm of torque at the knee joint. The prosthesis prototype weighed approximately 4.3 kg (9.5 lb), not including the mass of the shoe or height adaptor shown.

The stair ascent and descent control system was tested on a unilateral transfemoral amputee subject. The previously described impedance parameters were manually tuned for this subject in order to achieve appropriate stair ascent and descent behaviors. The amputee subject was a 23 year old man whose right side transfemoral amputation was the result of a traumatic injury. At the time of the experiments, he was 5 years post-amputation, and his daily use prosthesis was an Otto Bock C-Leg knee and a Freedom Innovations Renegade ankle/foot (i.e., a microprocessor-modulated damping knee, and a carbon fiber ankle/foot). In order to form a baseline for evaluation of the amputee subject's gait, kinematic data were also collected on 10 healthy male subjects with a mean age of 26.8 years (std. dev. 4.5 yrs.). Specifically, motion capture data were collected during both stair ascent and stair descent on a wooden 8-step staircase with 6.5" risers and 10" runners. Kinematic data were recorded with motion capture using a 12 camera Optitrack system from NaturalPoint. Marker data was collected at 120 Hz and converted to a skeletal model within NaturalPoint's ARENA software environment and exported as a BVH file resampled to 100 Hz. Sagittal plane joint angles were then extracted from the BVH files using MATLAB. Prior to testing, approval was received from the Vanderbilt University Institutional Review Board and all subjects gave informed consent, including permission for the publication of video and photographs.

Each subject ascended and descended the staircase in 10 trials. The second and third steps with each limb were used for analysis from each trial, totaling 20 strides for both ascent and descent for each subject. The same procedure was used for the amputee subject, although the use of a hand rail was allowed on the subject's sound side. For the amputee subject, trials were performed first with his daily use prosthesis (where he was instructed to attempt a step-over-step strategy for stair ascent, compensating for the lack of knee extensive torque with excessive hip extensive torque and by using the hand rail) and then with the powered prosthesis. It is important to note that the subject indicated that his preferred method of stair ascent with his daily-use prosthesis was to ascend each step with only his sound side. However, this method was selected for the comparison, since like the other cases (healthy and powered prosthesis), it represents step over step walking, and therefore arguably represents a fairer basis for comparison. For stair descent with the daily-use prosthesis, the subject chose a strategy in which the prosthetic heel is placed approximately half a foot length from the edge of the step and the foot rolls over the edge of the step, effectively using the interface between the stair edge and foot as a proxy for the ankle joint.

A. Results—Stair Ascent

Figure 33:
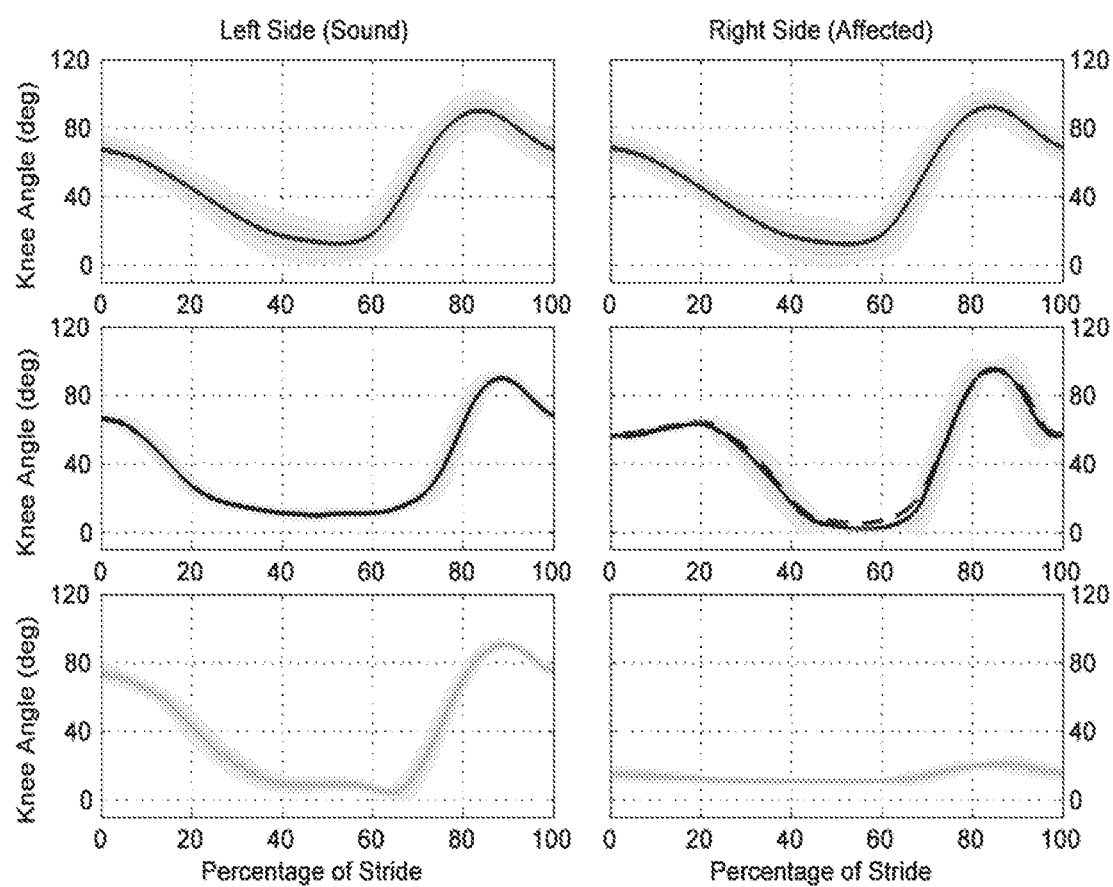
FIG. 33 shows plots of kinematics for the knee angle in stair ascent for healthy subjects, a subject using a prosthesis in accordance with the various embodiments, and a subject utilizing a passive prosthesis.
Figure 34:
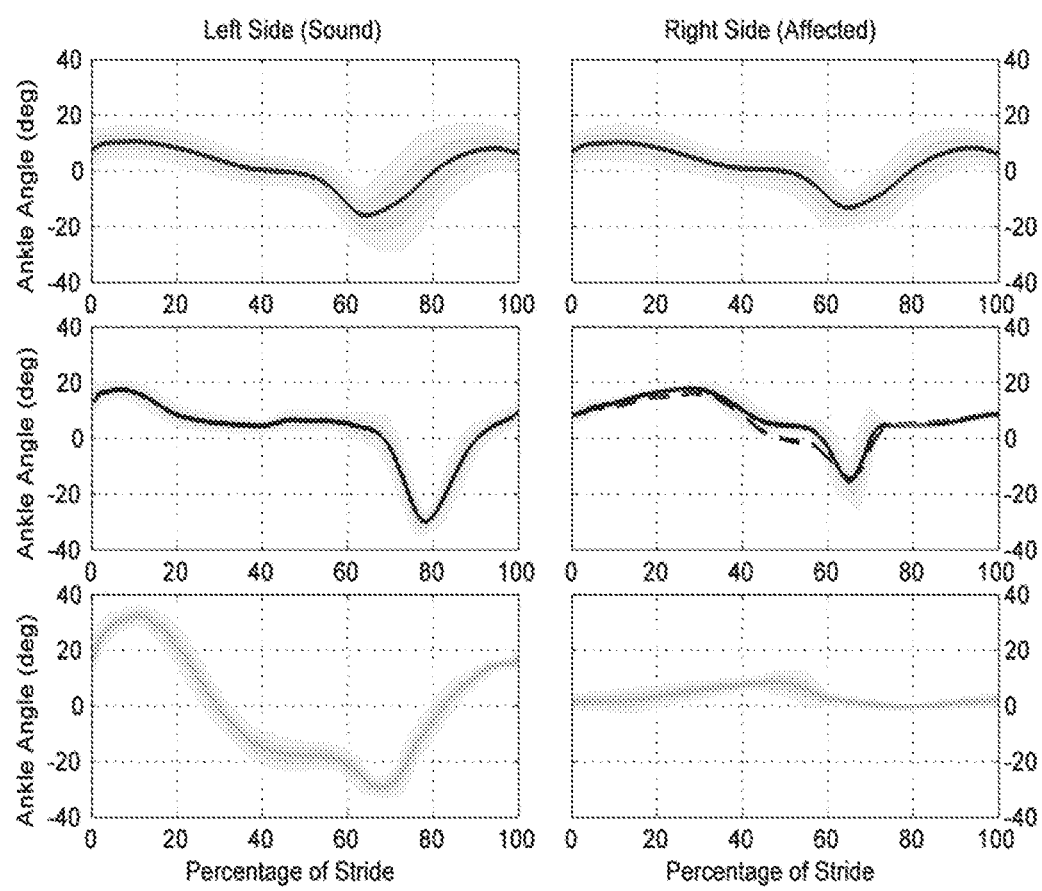
FIG. 34 shows plots of kinematics for the ankle angle in stair ascent for healthy subjects, a subject using a prosthesis in accordance with the various embodiments, and a subject utilizing a passive prosthesis.

FIGS. 33 and 34 show the knee and ankle joint angles versus stride for stair ascent for the three experimental cases previously described. In FIG. 33, the top row shows the left and right average knee joint angle from the 10 healthy subjects, wherein each healthy subject dataset represents 20 strides, the middle row is the average left (intact) and right (prosthetic) knee joint angle over 20 strides from the amputee subject with the powered prosthesis and previously described stair ascent controller, and the bottom row is the average left (intact) and right (prosthetic) knee joint angle over 20 strides from the amputee subject with his daily use passive prosthesis. Since the ground reaction force was not measured in these experiments, mean curves for each healthy subject were computed by parsing the strides through manual selection of heel contact. This point was determined by the small but sharp inflection present in the ankle angle at heel strike.

The same plots for the ankle joint are shown in FIG. 34. Since the powered prosthesis measures (and logs) the internally measured values for the knee and ankle angles, the mean curves corresponding to the joint angles measured internally in the prosthesis are also plotted as dashed lines on the subject's prosthetic side. Because ground contact is detected by a load threshold in the powered prosthesis, actual ground contact is made for some duration of time in the pre-landing phase (Phase 4) before the prosthesis transitions to Phase 0. As a result, a temporal offset was applied to the internal prosthesis signal to match the parsing of strides from the motion capture data.

Additionally, it should be noted that there is a small but noticeable difference between the motion capture ankle angle and the angle measured internally by the powered prosthesis. This discrepancy arises from the fact that the sole of the prosthetic foot is a stiff carbon fiber spring. As a result, during high torque activities such late-stance and push-off there is a small amount of flexion in the prosthetic foot. This flexion will cause the ankle angle, as measured by a motion capture system assuming a rigid body model of the foot, to drift towards dorsiflexion (for a torque in plantarflexion). For a pure carbon fiber ankle-foot complex (such as the subject's daily-use prosthesis), this flexion is precisely what is measured as the ankle angle.

B. Results—Stair Descent

Figure 35:
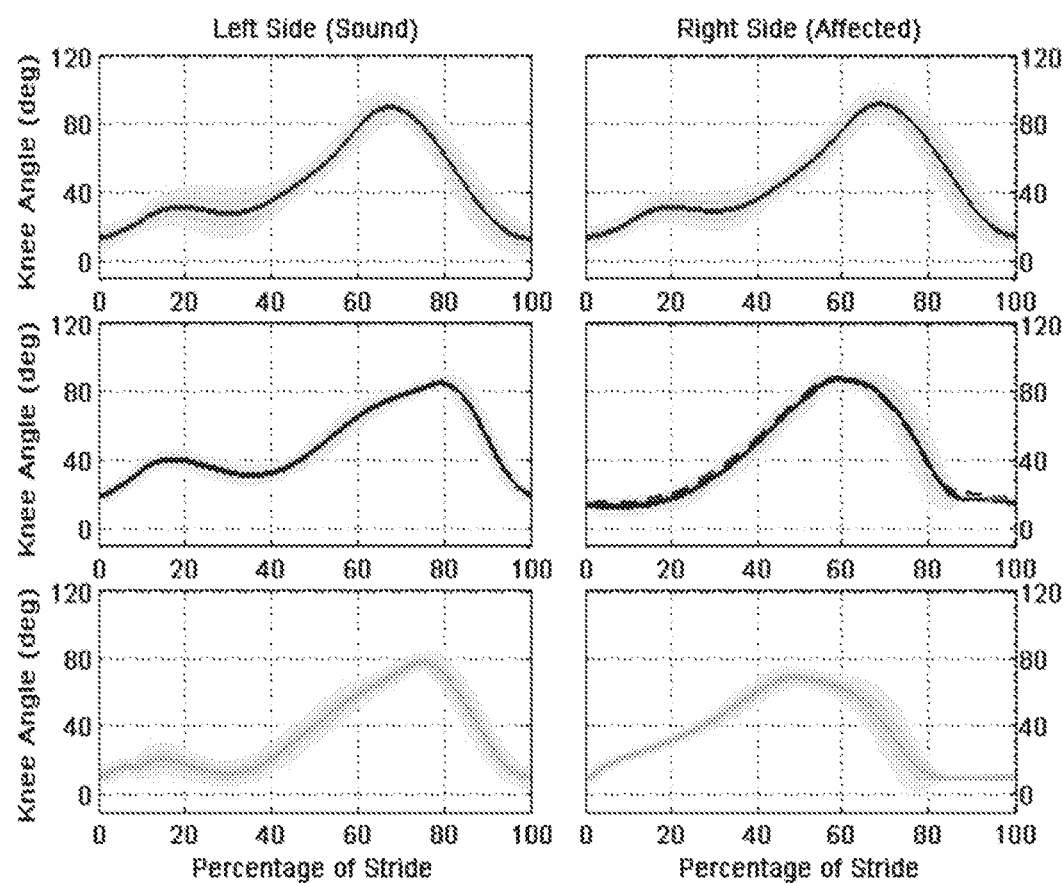
FIG. 35 shows plots of kinematics for the knee angle in stair descent for healthy subjects, a subject using a prosthesis in accordance with the various embodiments, and a subject utilizing a passive prosthesis.
Figure 36:
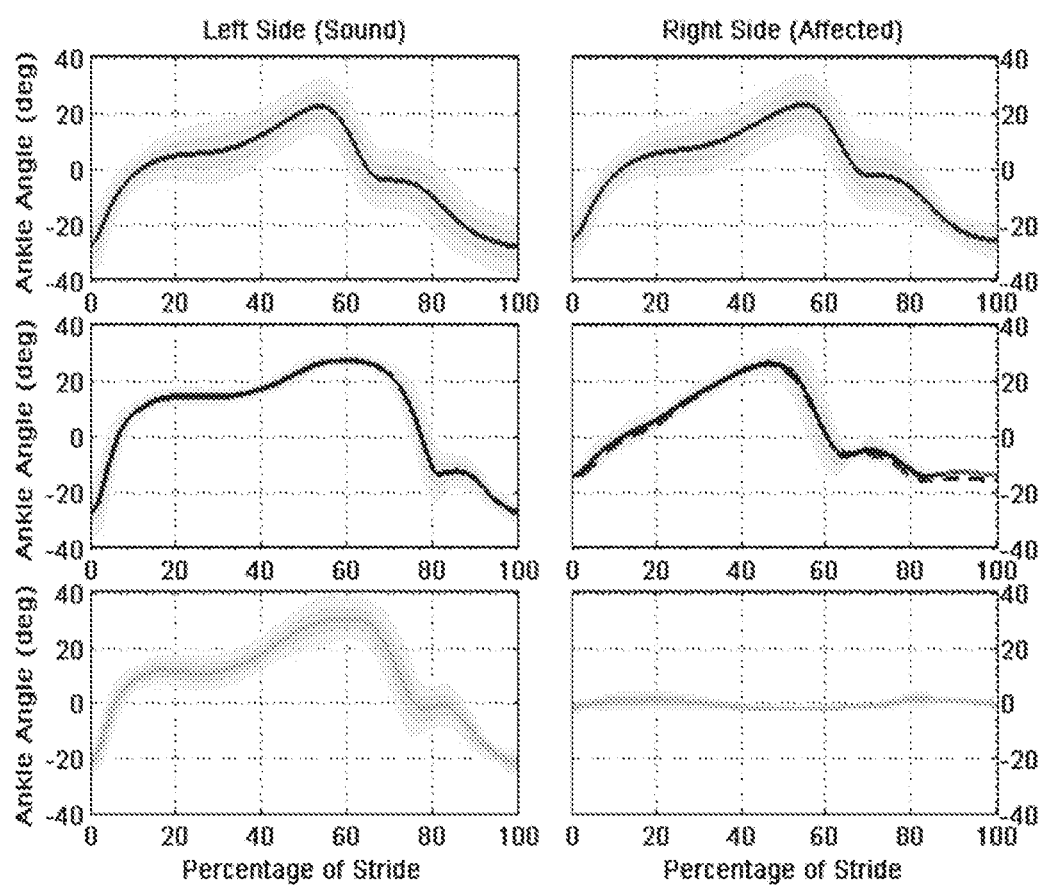
FIG. 36 shows plots of kinematics for the ankle angle in stair descent for healthy subjects, a subject using a prosthesis in accordance with the various embodiments, and a subject utilizing a passive prosthesis.

Stair descent knee and ankle kinematics are shown in the same form as for stair ascent in FIGS. 35 and 36 (also for 20 strides in all plots, and for 10 subjects in the healthy subject case). Again the internal measure of the powered prosthesis knee and ankle angles are plotted in dashed lines on the appropriate plots. Another temporal offset was applied to the internal signals to account for a different load threshold in this controller. Since there is no significant push-off in stair descent, large ankle torques are not present, and consequently there is no discrepancy in the two ankle angle measurements.

It is important to note the limitations of using averaged kinematic data across subjects as a standard for evaluating gait. Firstly, averaging the mean curves of each subject with respect to either time or normalized time (in terms of percentage of stride) can artificially reduce peaks in the data. For instance, if the instant of peak swing knee flexion varies from subject to subject, this will result in a smearing of the average peak knee flexion, producing what appears to be a wider, softer swing phase. Additionally, one would expect the averaged data to exhibit an increased symmetry between limbs, assuming that kinematic anomalies specific to each subject are equally distributed between the right and left limbs. In light of these issues, it is important to remember that the healthy subject data plotted in FIGS. 33, 34, 35, and 36 depict gait cycles that were never performed by a single individual.

Despite these limitations, reasonable evaluations of a particular gait cycle can still be made by comparing to these averaged data. It is clear from the stair ascent data in FIGS. 33 and 34 that the powered prosthesis provides a significantly better approximation of healthy joint kinematics than the passive knee and ankle counterparts (i.e., comparing the data in the right column of these respective figures). In stair descent, the passive and powered knees perform similarly (right column of FIG. 35), although the powered ankle clearly provides a significantly better approximation of healthy ankle behavior than the passive ankle (right column of FIG. 36).

C. Analysis—Stair Ascent

As depicted in FIG. 33, the knee angle of the powered prosthesis in stair ascent contains all the essential features of biomechanically normal stair ascent. There is a net knee extension in stance (occurring between 20% and 40% of the stride) and knee flexion in swing comparable to the healthy data (approximately 90° of knee flexion). However, the stance knee extension for the powered prosthesis appears slightly late relative to the healthy subject data. Additionally, the amputee subject's sound side stance knee extension appears to occur earlier than in the healthy subject data. This asymmetry occurs due to a slight pause in the amputee subject's gait as he checks the position of the prosthetic foot on the step and prepares for the transition to Phase 0, the stance phase where the prosthetic knee extends. The reason for this pause is due in part to the lack of proprioception on the amputee's affected side. Extra care and confirmation is therefore needed on the part of the amputee to confirm that the limb is configured in a safe way for the next step. If the pause were removed from the parsing of the stride, the knee kinematics would match extremely closely to the healthy average.

The ankle kinematics (FIG. 34) for the powered prosthesis also exhibited similar trends to that of the healthy subjects, although there was less symmetry in this case between the amputee subject's sound and affected sides. Specifically there was a heightened plantarflexion of the sound side ankle, though its peak of −30° is still within approximately 2 standard deviations of the healthy subject data. This peak suggests some sound-side compensation when using the powered prosthesis, although the extent of (kinematic) compensation appears to be considerably less than when the subject used his daily-use prosthesis. Additionally the early portion of the stance phase of the sound ankle showed evidence of vaulting, as the ankle plantarflexes at 30% of stride instead of 60%.

With regard to the characteristics of the passive prosthesis in stair ascent, a lack of power generation capability largely precludes net knee extension during stance phase, and so the amputee subject adopted a strategy of hip circumduction in order to achieve reciprocal stepping in this case. Specifically, the subject placed the prosthetic foot on the subsequent step, and with the knee mostly straight on the step above him, he made an extended and exaggerated ankle push-off, along with significant assistance from the sound side hand rail (see video included in the supplemental material). Although joint torque was not measured in these experiments, it is evident that the subject was forced to use excessive hip torque to vault over the passive device.

D. Analysis—Stair Descent

Since the knee acts primarily as a damper in stair descent, the subject's passive knee prosthesis is able to provide a high degree of functionality for this activity. Indeed, both the passive and powered knees provide fairly good facsimiles of healthy knee joint kinematics during stair descent. In both cases, however, there is a notable lack of early stance knee flexion (i.e., loading response) on the affected side. Although the framework of the powered prosthesis does allow for such stance knee flexion, the authors chose not to enable this feature, since it was effectively present via the compliance in the socket interface. An essential difference between the powered and the passive prostheses was the speed of stance knee flexion. Although the degree of damping in both the passive and powered prostheses can be adjusted (meaning that either one could be tuned to be faster or slower), the reason that the powered prosthesis exhibits a steeper knee flexion slope in descent (which more closely matches the healthy subject data) is because the total descent in the powered prosthesis is split into two portions. In the first portion of stance the descent is due to ankle flexion (Phase 0). After the ankle has dorsiflexed sufficiently, the controller transitions to Phase 1 and the knee flexes, continuing the descent. This damped ankle flexion is impossible in the case of the passive carbon fiber ankle-foot complex because it cannot actively plantarflex in anticipation of a descending forefoot strike. The difference is shown clearly in the ankle kinematics, where an initial ankle angle of almost −20° is achieved by the powered prosthesis before forefoot strike. Because the user must position the middle of the passive prosthetic foot over the edge of the step in order to allow knee flexion for descent, it is impossible to supply a moment to the ankle in stair descent, and, as a result, the ankle remains almost entirely motionless during the gait cycle. Thus, although the passive prosthesis enables effective stair descent, it could be argued that the passive prosthesis provides a less stable platform, since the prosthetic foot is not flat on the ground while the knee flexes in descent.

In summary, the experimental results above indicate that a powered prosthesis with a stair ascent controller configured in accordance with the various embodiments provides knee and ankle joint kinematics during stair ascent that are considerably more reflective of healthy knee and ankle joint kinematics, relative to a passive prosthesis. Further, experimental results of stair descent indicate that both passive prostheses and powered prostheses, configured in accordance with the various embodiments, provide appropriate knee joint kinematics during stair descent, while such powered prosthesis provides ankle joint kinematics considerably more reflective of healthy joint kinematics, relative to a passive ankle joint.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A non-transitory computer-readable medium comprising a plurality of instructions for causing a controller device of a lower limb device to perform the method comprising:

selecting one of a plurality of states of a finite state model defining a stair descent controller to yield a current state;

operating a motor of a powered knee joint of the lower limb device and a motor of a powered ankle joint of the lower limb device according to the current state of the stair descent controller;

collecting real-time sensor information from at least an inertial measurement unit and a position sensor for angle measurements of the powered knee joint;

based on the real-time sensor information for the lower limb device and a transition trigger for the current state, transitioning from a current state to a subsequent state in the finite state model;

computing an estimate of an orientation with respect to gravity of a thigh associated with the powered knee joint based on the real-time sensor information from the at least one inertial measurement unit;

operating the motor of a powered knee joint of the lower limb device and the motor of a powered ankle joint of the lower limb device according to the subsequent state of the stair descent controller; and repeating the operating the motors of the lower limb device at a subsequent state, the transitioning, and the computing until a criteria for exiting the stair descent controller is met, wherein the criteria is met when the estimate indicates an absence of thigh flexion for a period of time.

2. The non-transitory computer-readable medium of claim 1, further comprising stored instructions for causing the controller to perform, prior to the selecting, the steps of:

computing an estimate of an orientation with respect to gravity of a thigh associated with the powered knee joint based on the real-time sensor information from the at least one inertial measurement unit and the position sensor; and initiating the stair descent controller when the estimate of the orientation with respect to gravity for the thigh associated with the powered knee joint indicates thigh flexion for a period of time.

3. The non-transitory computer-readable medium of claim 1, wherein the operating of the motor of the powered knee joint and the motor of the powered ankle joint according to the current phase comprises performing, for each one of the powered knee joint and the powered ankle joint:
- identifying a stiffness coefficient, a damping coefficient, and an equilibrium angle pre-associated with the current phase; and
- controlling the motor to cause the output torque according to a pre-defined relationship between the output torque, an angular position, and an angular velocity that is based on the real-time sensor information, the stiffness coefficient, the damping coefficient, and the equilibrium angle.

4. The non-transitory computer-readable medium of claim 1, wherein the finite state model comprises a swing extension phase, a forefoot strike phase, a stance knee flexion phase, and a swing flexion phase and wherein the plurality of sensors further comprises a load sensor,
- wherein the transition trigger from the swing extension phase to the forefoot strike phase is detecting, by the load sensor, that a load on the lower limb device exceeds a threshold,
- wherein the transition trigger from the forefoot strike phase to the stance knee flexion phase is detecting that an angle of the powered ankle joint meets a threshold phase,
- wherein the transition trigger from the stance knee flexion phase to the swing flexion phase is detecting, by the load sensor, that the load on the lower limb device falls below the threshold, and
- wherein the transition trigger from the swing flexion phase to the swing extension phase is detecting that an angular velocity for the powered knee joint inflects.

5. The non-transitory computer-readable medium of claim 1, wherein the estimate is further based on at least one of:
- an estimation of a location of a segment of the lower limb device or a user through the at least one inertial measurement unit;
- a joint angle or angular velocity measurements from at least one of the plurality of sensors;
- a measurement of a degree of load or moment bearing in the lower limb device from a load sensor in the plurality of sensors, wherein the measurement of a degree of load is provided by a load sensor; or
- input received from a sensor.

* * * * *